US006171614B1

United States Patent
Chaikof et al.

(10) Patent No.: US 6,171,614 B1
(45) Date of Patent: Jan. 9, 2001

(54) SYNTHESIS OF GLYCOPHOSPHOLIPID AND PEPTIDE-PHOSPHOLIPID CONJUGATES AND USES THEREOF

(75) Inventors: Elliot L. Chaikof, Donwoody; Lijun Sun, Marietta, both of GA (US)

(73) Assignee: Emory University, Alanta, GA (US)

( * ) Notice: Under 35 U.S.C. 154(b), the term of this patent shall be extended for 0 days.

(21) Appl. No.: 09/514,348

(22) Filed: Feb. 28, 2000

Related U.S. Application Data

(62) Division of application No. 08/729,928, filed on Oct. 15, 1996, now Pat. No. 6,071,532.

(51) Int. Cl.[7] .................................................. A61K 9/127
(52) U.S. Cl. ..................... 424/450; 424/1.21; 424/9.321; 424/9.51; 424/417; 424/94.3; 514/2; 514/8; 514/21; 514/23; 514/53; 514/54; 530/402; 530/810; 536/26.1; 536/120; 554/79; 935/54; 428/402.2
(58) Field of Search ..................................... 424/450, 1.21, 424/9.321, 9.51, 417, 94.3; 436/829; 428/402.2; 935/54; 514/2, 8, 21, 23, 53, 54; 530/402, 810; 536/26.1, 120; 554/79

(56) References Cited

U.S. PATENT DOCUMENTS

| | | | |
|---|---|---|---|
| 4,624,919 | * 11/1986 | Kokusho et al. | 435/74 |
| 5,354,853 | * 10/1994 | Staveski et al. | 536/17.1 |
| 5,512,671 | * 4/1996 | Piantadosi et al. | 536/26.1 |

FOREIGN PATENT DOCUMENTS 0 719 778 A1 * 11/1995 (EP) .............................. C07H/15/10

OTHER PUBLICATIONS

Brezesinski, G. et al. "Influence of either linkages on the structure of double–chain phospholipid monolayers," Chem. and Phys. of Lipids (1995) 74:145–157.*

Chaikof, Elliot L., "Biomaterials that imitate cell microenviroments," Chemtech (1996) 26:17–22.*

Charych, Debroah and Nagy, Jon O., "Artificial cell membranes for dianostics and therapeutics," Chemtech (1996) 24–28.*

Haensler, Jean and Schuber, Francis, "Influence of the galactosyl ligand structure on the interaction of galactosylated liposomes with mouse peritoneal macrophages," Glycoconjugate Journal (1991) 8:116–124.*

O'Brien, David F., "Polymerization of Supramolecular Assemblies," Trends In Polymers (1994) 2:183–188.*

Tang, P.W. et al., "Novel Approach to the Study of the Antigenicities and Receptor Functions of Carbohydrate Chains of Glycoproteins," Biochemical and Biophysical Research Communications (1985) 132(2):474–480.*

Wang, P. et al., "Synthesis of Phospholipid–Inhibitor Conjugates by Enzymatic Transphospharidylation with Phospholipase D," J. Am. Chem. Soc. (1993) 115:10487–10491.*

Wiesmüller, K–H et al., "Solid phase peptide synthesis of lipopeptide vaccines eliciting epitope–specific B–, T–helper and T–killer cell response," Int. J. Peptide Protein Res. (1992) 40:255–260.*

* cited by examiner

*Primary Examiner*—Gollamudi S. Kishore
(74) *Attorney, Agent, or Firm*—Keil & Weinkauf

(57) ABSTRACT

The present invention provides glycophospholipid and peptide-phospholipid conjugates comprising a phospholipid moiety and a saccharide or peptide moiety joined by an ether linkage comprising a secondary or tertiary amine. The conjugate structure of the invention comprises a flexible spacer arm between the phospholipid and saccharide or peptide moieties which, being variable in length, serves to optimize saccharide or peptide bioactivity. This invention further provides a method for the synthesis of such conjugates comprising the step of reductive amination. The method is efficient, economical and provides a high yield of product. Glycophospholipid and peptide-phospholipid conjugates of the invention can be incorporated and, optionally, chemically polymerized in self-assembling systems such as membranes, bilayers, films, liposomes and the like, and find utility diagnostically and therapeutically in medical and immuno-biological applications.

20 Claims, No Drawings

SYNTHESIS OF GLYCOPHOSPHOLIPID AND PEPTIDE-PHOSPHOLIPID CONJUGATES AND USES THEREOF

CROSS-REFERENCE TO RELATED APPLICATIONS

This application is a division of Ser. No. 08/729,928 filed Oct. 15, 1996 now U.S. Pat. No. 6,071,532.

ACKNOWLEDGEMENT OF GOVERNMENT FUNDING

The invention was partially made with Government support under Grant No. N00014-95-1-1116 (subgrant No. G-33-V03-G1) awarded by the Office of Naval Research. The United States Government has certain rights in this invention.

1. Field of the Invention

The present invention relates generally to a glycophospholipid or peptide-phospholipid conjugate and to a method of synthesizing said phospholipid conjugate upon interaction of a phospholipid derivative with an activated saccharide, a nucleoside or a peptide. The present invention further relates to the incorporation of said phospholipid conjugate into a biological structure, to a pharmaceutical composition comprising a glycophospholipid or peptide-phospholipid conjugate, and to the use of a glycophospholipid or a peptide-phospholipid conjugate in medicinal and therapeutic indications.

2. Background of the Related Art

As self-organizing noncovalent supramolecular assemblies, membranes have offered a model for molecular engineering. Phospholipids differing in chemical composition, saturation, and size have been utilized as building blocks in the design of lipid-based cylinders, cubes, and spheres which have found applications both in drug delivery and as templates for composite structures [Fuhrhop et al. in *Membranes and Molecular Assemblies: Synkinetic Approach*, (1994) Royal Society of Chemistry, Cambridge, UK]. Likewise, recent approaches directed at the design of advanced materials for tissue engineering have emphasized the adhesion of cells on synthetic surfaces functionalized with epitopes derived from extracellular matrix proteins [Martin et al. (1982) J. Biol. Chem. 257:286–288; Shek et al. (1983) Immunology 50:101–106]. Polymerizable lipid amphiphiles, comprising lipids modified to contain reactive groups in distinct locations, provide opportunities to prepare such novel materials useful in diagnostics, drug delivery, surface modifications, etc. [O'Brien, Trends in Polymers (1994) 2:183–188].

Biomolecular recognition in multicellular systems is achieved by the presence of both integral proteins and carbohydrates which act as either ligands or receptors for neighboring cells, matrix, or soluble factors [Yeagle (1992) "The Structure of Biological Membranes," CRC Press, Boca Raton, Fla., USA]. Optimization of these receptor-ligand interactions is predicated upon lateral and rotational diffusion of both lipids and other macromolecules within the membrane suprastructure. Together, these structural features dictate, at least in part, the interaction of a cell with its surrounding microenvironment-interactions which bioengineers have sought to mimic in the rational design of biologically functional materials.

There are several classes of membrane lipids. The most abundant membrane lipids are the polar phospholipids, containing phosphorus in the form of phosphoric acid groups. The major phospholipids found in membranes are the phosphoglycerides, which contain two fatty acid molecules esterified to the first and second hydroxyl groups of glycerol. The third hydroxyl group of glycerol forms an ester linkage with phosphoric acid. The most abundant phosphoglycerides are the closely related phosphatidylethanolamine, phosphatidylcholine, phosphatidylserine and phosphatidylinositol. Phosphoglycerides are amphipathic, having a polar, hydrophilic "head" (phosphoric) group and nonpolar, hydrophobic tails.

Methods for synthesizing glycophospholipid conjugates are known in the literature. In some methods, a saccharide is combined with a phosphatidyl nitrogenous base through reductive amination. For example, a saccharide, in the form of a reducing sugar, is converted into a corresponding alditol by periodate oxidation and conjugated to a phosphatidylethanolamine derivative to form an imine intermediate, which is then reduced in the presence of sodium cyanoborohydride to produce a stable amino linkage [Tang et al. (1985) Biochem. Biophys. Res. Comm., 132:474–480]. The problem associated with this method of synthesizing glycophospholipid conjugates is that the ring structure of the reducing terminus of the saccharide is destroyed. Destruction of a functional group in the saccharide structure lowers the reactivity of the saccharide molecule and leads to changes in the biological activity of any glycolipid conjugates produced therefrom. Another problem with this method of synthesis is the lack of economy and/or efficiency between reactant equivalences in the lipid-saccharide conjugation reaction.

Glycolipid conjugates have also been prepared biochemically using enzyme preparations. For example, a specific type of phospholipase D [Kokusho et al., U.S. Pat. No. 4,624,919, issued Nov. 25, 1986; Shuto et al. (1988) Chem. Pharm. Bull., 36:5020–5023] has been used to facilitate the transfer of the phosphatidyl moiety from phosphatidylcholine to a primary hydroxyl group of a saccharide. However, the problem associated with this biochemical method of preparing glycophospholipid conjugates is that this method allows the preparation of only glycophospholipid conjugates having a fixed, non-modifiable distance between the phospholipid moiety and the saccharide residue. Undue proximity between the phospholipid and the sugar residues exerts stearic limitations and possible hindrance with respect to utilities associated with incorporation of synthesized glycolipids into membrane structures and their biological functionings.

The synthesis of a phospholipid-galactose conjugate has been reported by Haensler et al. (1991) (Glycoconjugate J. 8:116–124). This method involves preparing 2'-carboxyethyl-1-thiogalactoside in four steps from commercially available peracetylated galactose. The carboxylic acid on the galactoside is further refunctionalized with 1,3-diamino-2-propanol via amidation. The derivatized galactose is then coupled to the N-hydroxysuccinimide ester of N-succinyl phosphatidylethanolamine. The linker between the phospholipid and the galactose in the final product contains a minimum of sixteen hydrocarbon, carbonyl and amide bonds. This procedure is not suitable if conjugates having a shorter linker are desired.

In other art, dicarboxymethylated glycolipids were prepared by methods known in the art for use as cell adhesion inhibitors [Martel et al. EP 0719787]. In yet other art, ether lipidnucleoside conjugates have been prepared and used to combat HIV-1 infections (Piantadosi et al., U.S. Pat. No. 5,512,671, Apr. 30, 1996).

Phospholipid-saccharide conjugates were also produced by the reaction of a phospholipid derivative with an activated saccharide to form a phospholipid-saccharide molecule joined by a diether linkage (Staveski et al., U.S. Pat. No. 5,354,853, issued Oct. 11, 1994). The diether linkage bridging the phospholipid and saccharide comprised a straight chain or branched alkyl group having from 1 to about 20 carbon atoms. However, one of the problems associated with this method is the extremely low yield of phospholipid-saccharide conjugate obtained by this process. For example, the yields obtained for the preparation of phospholipid-monosaccharide conjugates were in the range of 0.7 to 6% of the starting amount of protected monosaccharide. Additionally, this method required a long time (approximately 4 days) for the preparation of a phospholipid-saccharide conjugate.

Methods are also available in the art for the synthesis of peptide-phospholipid conjugates, e.g., with enzymatic transphosphatidylation [Wang et al. (1993) J. Am. Chem. Soc. 115:10487–10491]. However, these methods present problems with lack of economy, efficiency and low yields, similar to those associated with the prior art methods for glycophospholipid is conjugates.

Thus, there is a need in the art for glycophospholipid and protein-phospholipid conjugates wherein the saccharide ring structure remains functionally intact and wherein the linkage joining the phospholipid and saccharide or peptide moieties constitutes a flexible spacer arm having a modifiable length and composition. There also exists a need for a method of synthesis of such glycophospholipid or peptide-phospholipid conjugates, wherein the method is highly efficient and economical and provides high yields of conjugate products and wherein the method is carried out easily under routine laboratory conditions.

These needs in the art are met by the present invention as disclosed herein.

SUMMARY OF THE INVENTION

It is an object of the invention to provide a glycophospholipid conjugate and a peptide-phospholipid conjugate comprising a phospholipid moiety and a saccharide moiety joined by an ether linkage comprising a secondary or tertiary amine and having the general formula

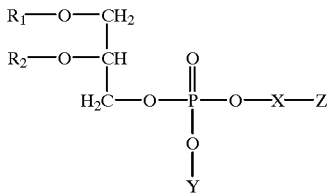

wherein
  $R_1$ and $R_2$ are independently selected from the group comprising straight or branched, unsubstituted or substituted, saturated or unsaturated, alkyl, alkenyl, alkynyl and aryl groups, and their corresponding acyl derivatives;
  Y is a cation;
  X is a secondary or tertiary amine linker, comprising two to twenty carbon atoms, wherein the substituent groups of the amine are selected independently from a group comprising a hydrogen, a straight or branched, unsubstituted or substituted alkyl, alkenyl, alkynyl and aryl groups; and
  Z is a saccharide, peptide or a functional derivative thereof.

In preferred embodiments of glycophospholipid conjugates of the invention, $R_1$ and $R_2$ are residues exemplified by, but not limited to, lauroyl, myristoyl, palmitoyl, palmitoleoyl, stearoyl, oleoyl, linoleoyl, arachidoyl, linolenoyl, arachidonoyl, diacetylenic, methacryloyl, acryloyl, dienoyl, sorbyl, lipoyl, styryl and the like. $R_1$ and $R_2$ may be the same or different residues.

Also, in preferred embodiments of the invention, the saccharide moiety used for the preparation of glycophospholipid conjugates can be a monosaccharide, a disaccharide, an oligosaccharide, a polysaccharide or a substituted derivative thereof. It is also contemplated by this invention that a saccharide may represent a saccharide moiety that resides as a component part of a larger molecule, for example, as the saccharide moiety of a nucleoside, a nucleotide, a polynucleotide, a DNA, an RNA, etc.

It is another object of the invention to provide glycophospholipid and peptide-phospholyid conjugate structures comprising a flexible spacer arm between phospholipid and the saccharide or peptide moieties which, being variable in length, serves to optimize saccharide bioactivity. In particular embodiments, the length of the spacer arm is defined in part by the selection of an appropriate diol or polyethyleneglycol molecule for attachment to a saccharide or peptide moiety prior to its interaction with a phosphatidylethanolamine moiety.

Glycophospholipid and peptide-phospholipid conjugates of the invention constitute a new class of amphiphiles having biomedical applications in the areas of drug and gene delivery, as well as in biomaterials and biosensors, including the creation of bioactive surfaces and structures.

It is a further object of the present invention to provide a method for the synthesis of a glycophospholipid or a peptide-phosphoslipid conjugate of the invention. This method is both efficient and economical and, additionally, provides a high yield of product. Glycophospholipid and peptide-phospholipid conjugates are synthesized by chemical and/or biochemical methods suitable for the formation of an amine ether covalent linkage between a phospholipid moiety and a functionalized saccharide or peptide molecule.

A glycophospholipid or peptide-phospholipid conjugate of the invention is synthesized upon conjugation of a phospholipid moiety with an activated saccharide or peptide, preferably an aldehyde-functionalized saccharide or peptide through formation of a covalent bond comprising an ether linkage having a secondary or tertiary amine. In a preferred embodiment of the invention, the method of synthesis involves: (a) the coupling of an activated saccharide or peptide with a diol; (b) the transformation of the remaining primary hydroxyl group to an aldehyde; (c) the reductive amination of the aldehyde with a phosphatidyl nitrogenous base; and (d) removal of protecting groups on the saccharide or peptide moiety. This method leads to the synthesis of a glycophospholipid or peptide-phospholipid conjugate in which the phospholipid and ssaccharide or peptide components are joined by an ether linkage comprising a secondary or tertiary amine. The overall yield of product from this method of synthesis ranges from 15–50%, depending on the nature of the saccharide or peptide and the length of the spacer-arm.

It is another object of the invention to incorporate the glycophospholipid and peptide-phospholipid conjugates of the invention into self-assembling systems, such as lipid monolayers useful for behavioral studies, for example, at air-water interfaces, or as biomembrane-mimicking structures, for example, liposomes useful, for example, as targeted carrier vehicles, or substrate supported membranes, useful, for example, for bioactivity assays.

It is also an object of the invention to provide a glycophospholipid or peptidephospholipid liposome preparation comprising a drug or therapeutic agent. Such liposomal preparations may be specifically targeted for a designated cell type or tissue. Liposomes carrying a drug or therapeutic agent to a specific location are useful diagnostically and/or therapeutically, for example, against disease, e.g., cancer, infectious diseases, etc. For example, this invention provides liposomes carrying nucleic acid derivatives (nucleosides, nucleotides, polynucleotides, DNA, RNA, etc.), protein, for example monoclonal antibodies, etc., vitamins, and the like.

In addition, this invention provides a pharmaceutical composition comprising a glycophospholipid conjugate or a peptide-phospholipid conjugate of the invention comprising a drug or therapeutic agent useful in targeted delivery and/or therapy.

In a particular embodiment of the invention, the saccharide moiety used for the preparation of a glycophospholipid conjugate is a polysaccharide or glycan, as exemplified by a heparin molecule. The heparin-phospholipid conjugate of the invention is useful, e.g., as a therapeutic agent, a pharmaceutical composition and a hemocompatibility agent for medical devices. In other embodiments, the polysaccharide used for the preparation of a glycophospholipid conjugate is heparan sulfate, chondroitin sulfate, dermatan sulfate or a polysaccharide derivative thereof.

This invention further contemplates the use of the method provided by the invention for the preparation of a new class of compounds comprising a nucleoside-phospholipid conjugate having an amine ether linkage bridging the phospholipid and nucleoside moieties. Such nucleoside-phospholipid conjugates are prepared by joining the saccharide component of a nucleoside or a nucleosidic derivative, such as a nucleotide, polynucleotide, DNA, RNA, etc., and a phospholipid nitrogen base with formation of an ether linkage comprising a secondary or tertiary amine.

In a particular embodiment of the invention are provided synthetic vaccines which are synthesized according to the method of the invention such that a phospholipid nitrogen base is joined by reductive amination to a peptidyl or saccharide epitope through formation of an ether linkage comprising a secondary or tertiary amine. Such phospholipid conjugates function as synthetic vaccines in eliciting the formation of immunoprecipitating antigen-specific polyclonal and monoclonal antibodies in vitro and in vivo.

BRIEF DESCRIPTION OF THE DRAWINGS

FIG. 1 presents a scheme illustrating the steps of the method used to synthesize a glycophospholipid conjugate. In this example, the starting reactants are α-1-chloro-2,3,4,6-tetra-O-benzyl-glucopyranoside and phosphatidylethanolamine. In step (i), an activated saccharide is coupled with a diol in the presence of $CdSO_3$ and $CaSO_4$. Step (ii) depicts the conversion of the remaining saccharide primary alcohol to a corresponding aldehyde in the presence of pyridinium dichromate (PDC). Step (iii) illustrates the reductive amination of the aldehyde with phosphatidylethanolamine in the presence of sodium cyanoborohydride. In step (iv) the protecting groups on the saccharide are removed to yield a glucopyranoside-distearoyl phosphatidylethanolamine conjugate. Bn=benzyl; n=1–18; PDC=pyridinium dichromate; DSPE=distearoyl phosphatidylethanolamine; $NaBH_3CN$=sodium cyanoborohydride; Pd—C=palladium on carbon.

FIG. 2 presents a scheme illustrating steps in a method useful for the synthesis of a nucleoside-phospholipid conjugate. In this example, the starting reactants are 4'5'-didehydro-5'-methoxy-adenosine and phosphatidylethanolamine. In the first step, the functional alcohol and amine groups are benzylated. The protected nucleoside is then converted to an aldehyde functionalized derivative at the 5' position. In the next step, the aldehyde activated nucleoside is interacted with phosphatidylethanolamine by reductive amination in the presence of sodium cyanoborohydride. The protecting groups are then removed to yield an adenosine-phosphatidylethanolamine conjugate. BnBr=benzylbromide; NaH=sodium hydride; Bn=benzyl; DSPE=distearoylphosphatidylethanolamine; $NaBH_3CN$=sodium cyanoborohydride; Pd—C=palladium on carbon; n=1–18.

FIG. 3 presents a scheme illustrating steps in a method useful for the synthesis of a peptide-phospholipid conjugate. In this example, the staring reactants are O-benzyl-glycylseryl-glycylalanylvaline and phosphatidylethanolamine. In the first step, the protected peptide is extended to contain a hydrocarbon chain of variable length by interacting the peptide with a hydroxy acid derivative of a diol where n=1–18 in the presence of DCC and N-hydroxysuccinimide. The peptidyl alcohol derivative is then oxidized to the corresponding aldehyde under a nitrogen atmosphere in the presence of pyridinium dichromate. In the next step is illustrated the reductive amination of the aldehyde moiety with phosphatidylethanolamine in the presence of sodium cyanoborohydride. The protecting groups are then removed to yield a peptide-phosphatidylethanolamine conjugate. En=benzyl; PDC=pyridinium dichromate; DSPE=distearoyl phosphatidylethanolamine; $NaBH_3CN$=sodium cyanoborohydride; Pd—C=palladium on carbon; DCC-dicyclohexylcarbodiimide.

DETAILED DESCRIPTION OF THE INVENTION

The following definitions are provided to remove any potential ambiguities as to the intent or scope of their usage in the specification and claims.

The term phospholipid, as used herein, refers to a class of compounds having a glycerol backbone which is alkylated or acylated at the $C_1$ and $C_2$ positions with lipid moieties and which is esterified at the $C_3$ position with phosphoric acid or a phosphoric acid derivative. Naturally occurring phospholipids contain fatty acid residues at the $C_1$ and $C_2$ positions while the phosphoric acid "head" group comprises a polar group. Phospholipids are classed according to their head group. In general, with respect to the invention, a phospholipid useful for the invention must contain a nitrogenous base having a free —NH— group, i.e., the nitrogen must be bonded to at least one hydrogen.

The term phospholipid nitrogenous base, as used herein, refers to a class of compounds having a glycerol backbone which is alkylated or acylated at the $C_1$ and $C_2$ positions with lipid moieties and which is esterified at the $C_3$ position with phosphoric acid derivative comprising a nitrogenous base. The nitrogenous base must have a free —NH— group, i.e., the nitrogen must be bonded to at least one hydrogen.

The term phosphatidyl nitrogenous base, as used herein, refers to a class of compounds having a glycerol backbone which is acylated at the $C_1$ and $C_2$ positions with lipid moieties and which is esterified at the $C_3$ position with phosphoric acid or a phosphoric acid derivative comprising a nitrogenous base. Phosphatidyl nitrogenous bases are classed according to their head alcohol group, the most abundant being phosphatidylethanolamine and phosphatidylcholine, which contain the alcohols ethanolamine and choline, respectively, on their polar heads. Each of these can contain different combinations of fatty acids. In general, with respect to the invention, a phosphatidyl nitrogenous base must contain a free —NH— group, i.e., the nitrogen must be bonded to at least one hydrogen.

The term a free —NH— group, as used herein, refers to an amine group wherein the nitrogen is bonded to a hydrogen.

The term saccharide, as used herein, refers to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Monosaccharides include, but are not limited to, ribose, 2-deoxy-ribose, glucose, mannose, xylose, galactose, fucose, fructose, etc. Disaccharides contain two monosaccharide units joined by a glycosidic linkage. Disaccharides include, for example, sucrose, lactose, maltose, cellobiose, and the like. Oligosaccharides typically contain from 2 to 10 monosaccharide units joined in glycosidic linkage. Polysaccharides (glycans) typically contain more than 10 such units and include, but are not limited to, molecules such as heparin, heparan sulfate, chondroitin sulfate, dermatan sulfate and polysaccharide derivatives thereof. The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc. A saccharide may also reside as a component part of a larger molecule, for example, as the saccharide moiety of a nucleoside, a nucleotide, a polynucleotide, a DNA, an RNA, etc.

The term glycophospholipid conjugate, as used herein, refers to the conjugation product between a phospholipid and a saccharide joined by an amine diether linkage. The phospholipid can be represented by any phosphoglyceride molecule having a free —NH— group. The saccharide molecule can be a mono-, di-, oligo- or polysaccharide that is capable of functioning as a reducing sugar and can reside as a component part of a larger molecule, for example, a nucleoside, a nucleotide, a polynucleotide, a DNA, an RNA, etc.

The term nucleoside-phospholipid conjugate, as used herein, refers to the conjugation product between a phospholipid and the saccharide component of a nucleoside (or nucleotide, polynucleotide, DNA, RNA, etc.) wherein the phospholipid and saccharide moieties are joined by an amine ether linkage.

The term peptide-phospholipid conjugate, as used herein, refers to the conjugation product between a phospholipid and a peptide, wherein the phospholipid and peptide moieties are joined by an amine ether linkage.

The term polymerizable amphiphile or polymerizable lipid, as used herein, refers to a lipid modified to contain a reactive group in a distinct location and capable of being assembled or polymerized as a lipid bilayer or as unilamellar or multilamellar vesicles.

The terms carrier or vehicle or carrier-vehicle or drug delivery system, as used herein, refer to a molecule having a lipophilic or amphiphilic character and capable of associating with a drug or therapeutic agent for the purpose of delivering said drug or therapeutic agent to a desired location.

The term reducing sugar, as used herein, refers to a saccharide capable of reducing such oxidizing agents as ferricyanide, hydrogen peroxide, or cupric ion.

The terms activated saccharide or peptide or activated saccharide or peptide derivative, as used herein, refer to a saccharide or peptide molecule that is in a state or condition rendering it capable of undergoing a chemical reaction.

The terms aldehyde-functionalized saccharide derivative or aldehyde-functionalized peptide derivative, as used herein, refer to a compound having the general formula

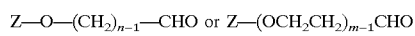

wherein n=1–18, m=3–250, and Z=a saccharide, peptide or a functionalized derivative thereof.

The term liposome, as used herein, refers to a microscopic sphere that is a closed, self-sealing, solvent-filled vesicle bounded by a single lipid bilayer. Once formed, liposomes are quite stable and may be recovered by dialysis, gel filtration chromatography or centrifugation. Liposomes having different internal and external environments can be readily prepared. Liposomes composed of synthetic lipids and/or lipids extracted from biological sources have been studied as models for biological membranes. Liposomes can be easily prepared such that a drug or a therapeutic agent (e.g., a protein (e.g., a monoclonal antibody) or a DNA) is entrapped or is electrostatically associated with the liposomal structure. Such drug- or agent-carrying liposomes can be targeted or made specific for a designated cell type or tissue.

The term polyethyleneglycol (PEG), as used herein, refers to a polymer of the general formula $H(OCH_2CH_2)_nOH$, where n is greater than or equal to 3 and, preferably, between 3 and 250.

The term drug, as used herein, refers to a substance other than food or water that is intended for use in the diagnosis, cure, mitigation, treatment or prevention of disease, or is intended to affect the structure or any function of the body of man or other animal.

The term therapeutic agent, as used herein, refers to a substance that is intended for use in effecting the cure or management of a disease.

The term nucleosidic derivative, as used herein, refers to a molecule, the structure of which comprises a nucleoside moiety, e.g., a nucleotide, a polynucleotide, DNA, RNA and the like.

The term peptide, as used herein, refers to an amino acid chain having a variable length, composition and structure, and embraces art-known terms such as oligopeptide, polypeptide, protein and the like.

The term epitope, as used herein, refers to any structural component of an antigen molecule which is known to function as an antigenic determinant by allowing the attachment of certain antibody molecules.

The term synthetic vaccine, as used herein, refers to a glycophospholipid or peptide-phospholipid conjugate of the invention wherein the conjugate comprises an epitope. In preferred embodiments, a synthetic vaccine refers to a peptide-phospholipid conjugate wherein said peptide comprises a synthetic peptide sequence related to an antigenic determinant (epitope) of a protein antigen coupled with a lipophilic carrier molecule, such as a phospholipid or phospholipid derivative. A synthetic vaccine functions immunologically in expected fashion in vitro and in vivo, as known in the art.

The present invention is directed to glycophospholipid and peptide-phospholipid conjugates joined by an ether linkage comprising an amine group. Such glycophospholipid and peptide-phospholipid conjugates represent a new class of amphiphiles having the structure

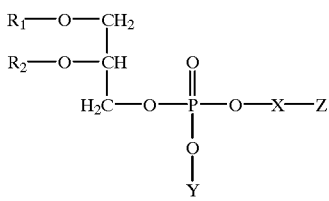

wherein $R_1$ and $R_2$ are independently selected from the group comprising straight or branched, unsubstituted or substituted, saturated or unsaturated alkyl, alkenyl, alkynyl and aryl groups, and their corresponding acyl derivatives;

Y is a cation;

X is a secondary or tertiary amine linker, comprising two to twenty carbon atoms, wherein the substituent groups of the amine are selected independently from a group comprising a hydrogen, a straight or branched, unsubstituted or substituted, saturated or unsaturated alkyl, alkenyl, alkynyl and aryl groups; and Z is a saccharide, peptide or a functionalized derivative thereof.

The cation, Y, includes, but is not limited to, a hydrogen ion, an alkali metal ion, an ammonium ion, a substituted ammonium ion, and the like.

The amino ether linkage joining the phospholipid and saccharide or peptide components comprises a secondary or tertiary amine comprising from two to twenty carbon atoms. This linkage constitutes a flexible spacer arm, serving to optimize saccharide bioactivity. The length of the spacer arm is easily adjusted by virtue of the reactants selected for the synthesis of the glycophospholipid or peptide-phospholipid conjugant. For example, a linker can be designed to have a desired dimension by selecting or synthesizing an appropriate alkyl diol/aldehyde to combine with a preselected or synthesized phosphatidyl nitrogenous base of an appropriate length. In specific embodiments, the spacer arm is defined in part by selection of a diol, $HO(CH_2)_nOH$, wherein n=1–18, or a polyethyleneglycol, $H(OCH_2CH_2)_mOH$, wherein m=3–250. In general, a shorter linkage is preferred in glycophospholipid and peptide-phospholipid conjugates destined for use in membrane associated functions, whereas a longer spacer arm is generally more appropriate in conjugates used for more polar indications, e.g., immunotargeting functions.

Further, the present invention is directed to a method of making a glycophospholipid or peptide-phospholipid conjugate of the present invention. This method comprises the step of conjugating a phospholipid moiety with a saccharide or peptide moiety through the formation of an ether linkage comprising a secondary or tertiary amine. In one embodiment of the invention, the method of synthesis involves: (a) coupling of an activated saccharide or peptide with a diol; (b) transformation of the remaining primary hydroxyl group to an aldehyde; (c) reductive amination of the aldehyde with phosphatidyl nitrogenous base; and (d) subsequent removal of protecting groups from the saccharide or peptide component. This process leads to the synthesis of a saccharide-phospholipid conjugate or a peptide-phospholipid conjugate joined by an ether linkage comprising a secondary or tertiary amine.

Phospholipid nitrogenous bases useful as starting reagents in the synthesis method of this invention must contain a free —NH— group in the polar "head" region. Such phospholipid nitrogenous bases may be obtained commercially or may be chemically and/or biochemically synthesized using routine methodology from a phospholipid and a hydroxylamine having a desired number of carbon atoms and functional amine and hydroxyl groups. For the synthesis of a desired phospholipid nitrogenous base, preferred starting phospholipid derivatives include those having fatty acids selected from a group comprising, for example, lauroyl, stearoyl, oleoyl, myristoyl, palmitoyl, palmitoyloleoyl, linoleoyl, arachidoyl, linolenoyl, arachidonoyl, etc., or other reactive groups such as diacetylenic, methacryloyl, acryloyl, dienoyl, sorbyl, lipoyl, styryl and the like. Preferred starting hydroxylamines include ethanolamine, N-alkyl-ethanolamine, serine, etc. The phosphatidyl nitrogenous base particularly preferred for use in the synthesis method of the invention is phosphatidylethanolamine or a synthetic derivative thereof having a modified number of carbon atoms.

Phospholipids having chemical variations in the hydrocarbon chains attached at the $C_1$ and $C_2$ positions of the glycerol moiety can influence lipid phase parameters, miscibility properties, etc. of the phospholipid molecules in bulk systems. Such hydrocarbon chain variations include chain length, chain unsaturation, chain branching and chain linkage. For example, the replacement of a carbonyl group by a methylene group (ester to ether linkage) leads to a reduction in hydrophobicity and enables a tighter chain packing close to the water surface. Also, the chain melting temperatures (Tm) of dialkylphospholipids in aqueous dispersion are slightly higher than the Tm values of the corresponding diacylphospholipids [Brezesinski et al. (1995) Chemistry and Physics of Lipids 76:145–157]. Nevertheless, both dialkylphospholipids and diacylphospholipids form stable monolayers on water. Thus, the present invention contemplates the use of diacylphospholipids as well as dialkylphospholipids.

The saccharide moiety used for the preparation of glycophospholipid conjugates of the invention can be a monosaccharide, a disaccharide, an oligosaccharide, a polysaccharide or a substituted derivative thereof. An example of a saccharide includes, but is not limited to, glucose, galactose, mannose, xylose, fructose, fucose, ribose, 2-deoxy-ribose, maltose, lactose, sialic acid, N-acetylgulcosamine, N-acetylgalactosamine, N-acetylneuraminic acid, galactosy-N-acetylglucosamine, acetylglucose, acetylgalactose, glucosamine, galactosamine, heparin, heparan sulfate, chondroitin sulfate, dermatan sulfate, and the like. It is also contemplated by this invention that a saccharide may represent a saccharide moiety that resides as a component part of a larger molecule, for example, as a saccharide moiety of a nucleoside, a nucleotide, a polynucleotide, a DNA, an RNA, etc.

The saccharide used in producing a glycophospholipid conjugate of the invention can be activated, for example, at the $C_1$ position using standard chemical techniques. For example, a saccharide can be activated as a glycosyl halide [Paulsen (1982) Angew. Chem. Int. Ed. 21:155–224], a glycosyl imidate [Schmidt et al. (1985) J. Carbo. Chem. 4:141–169]; a thio-glycoside [Fugedi et al. (1987) Glycoconjugate J. 4:97–108]; an alkenyl glycoside [Fraser-Reid et al. (1988) J.C.S. Chem. Comm. 823–825] or an oxazoline [Colon et al. (1991) Tet. Letters 32:4447–4450]. The remaining hydroxyl groups on the saccharide molecule are blocked by protecting groups by art known methods. In a particular embodiment of the invention, it is preferred that the activated saccharide comprise a reactive aldehyde group, which undergoes reductive amination by a nucleophilic amine residing in a phosphatidyl nitrogenous base.

In a preferred embodiment of the present process, conjugation is produced by combining a phospholipid with an activated saccharide or peptide moiety in an organic solvent milieu. The conjugation reaction proceeds by reduction in the presence of an ammonia derivative, i.e., reductive amination. The reduction can be accomplished catalytically, e.g., in the presence of nickel, etc., or by the use of a coupling agent appropriate for the aldehyde group of the functionalized saccharide, such as sodium cyanoborohydride ($NaBH_4CN$) or the like. The organic solvent medium is selected to be compatible with the phospholipid, the activated saccharide or peptide and the coupling agent. The coupling reaction is allowed to proceed at a temperature and for a time sufficient to permit covalent conjugation between the saccharide or protein and the phospholipid component.

In a preferred embodiment of the method of the invention as illustrated in FIG. 1, the activated saccharide used as a starting reagent is a protected, halo-derivative of the saccharide as exemplified by 1-α-chloro-2,3,4,6-tetra-O-benzyl-glucopyranoside. As shown in FIG. 1 illustrating a particular embodiment of the invention, the protected chloro-glucopyranoside is first coupled with an alkyl diol (exemplified by decanediol) and then the remaining primary hydroxyl group is transformed into a corresponding aldehyde. Next, the aldehyde undergoes reductive amination with a phosphatidyl nitrogenous base (exemplified by phosphatidylethanolamine). In the last step of the method, the protecting groups on the saccharide component are removed. The product of this synthesis method of the invention is a glycophospholipid conjugate in which the phospholipid and saccharide components are joined in a diether linkage comprising a secondary or tertiary amine.

The protection and deprotection of functional groups is a strategy employed in the present invention to block participation of these groups in an ongoing chemical reaction. Such protecting groups are well known in the art and can be readily removed, for example, by chemical or enzymatic hydrolysis, reduction or hydrogenation, or by UV irradiation, etc. Suitable hydroxy-protecting groups may be, for example, acyl groups such as acetyl, trichloroacetyl, phenoxycarbonyl, benzyloxycarbonyl, benzhydryloxycarbonyl, trityloxycarbonyl and 2,2,2-trichloroethoxycarbonyl, ether groups such as methoxymethyl, benzyloxymethyl, allyl, benzyl, p-methoxybenzyl, p-nitrobenzyl, benzhydryl, trityl or triorganosilyl groups such as tri($C_1$–$C_6$) alkylsilyl (e.g., trimethylsilyl, triethylsilyl, triisopropylsilyl, isopropyldimethylsilyl, t-butydimethylsilyl, methyldiisopropylsilyl or methyldi-t-butylsilyl), t-butyl-diphenylsilyl, triarylsilyl (e.g., triphenylsilyl, tri-p-xylylsilyl) or triaralkylsilyl (e.g., tribenzylsilyl). Examples of these and other suitable hydroxy-protecting groups and methods for their formation and removal are known in the art. See, for example, *Protective Groups in Organic Synthesis*, second ed., T. W. Greene and P. G. M. Wuts, John Wiley & Sons, New York, 1991, Chapter 2 and references therein.

The overall yield for the synthesis of a glycophospholipid conjugate according to the method of the invention is in the range of about 15 to 52% of the starting amount of a protected, activated monosaccharide. These yields are higher than prior art values by about an order of magnitude. For example, phospholipid-saccharide conjugates prepared by the prior art method of Staveski et al. (U.S. Pat. No. 5,354,853) gives yields in the range of <1.0 to 6.0% of the starting amount of a protected, activated monosaccharide.

Specifically, the yield at each step of the method for the synthesis of a conjugate between phosphatidylethanolamine and glucose is documented in Table 1.

TABLE 1

Yield of Glucopyranoside-distearoylphophatidylethanolamine

| | Yield (%) | |
|---|---|---|
| | n = 10 | n = 7 |
| Compound 1 | 100 | 100 |
| Compound 2 | 86 | 75 |
| Compound 3 | 74 | 74 |
| Compound 4 | 85 | 95 |
| Compound 5 | 73 | 77 |
| Overall (1 → 5) | 39.5 | 40.6 | n = number of carbon atoms in a diol [i.e., $HO(CH_2)_nOH$] coupled to the saccharide at carbon 1.
Compound 1 = protected, activated saccharide, i.e., 1-chloro-2,3,4,6-tetra-O-benzylglucopyranoside.
Compound 2 = alcohol derivative of compound 1.
Compound 3 = aldehyde derivative of compound 2.
Compound 4 = protected, glycophospholipid conjugate.
Compound 5 = glycophospholipid conjugate.

An overall yield of phospholipid-glucose conjugate of about 40% was obtained with the method of the invention. In contrast, for the same monosaccharide, glucose, the method of Staveski et al., supra, produced a phospholipid-glucose conjugate at a yield of approximately 5.6% of the starting amount of protected, activated glucose.

Similarly, for the synthesis of a glycophospholipid conjugate with galactose, the method of the invention offers a yield of between 32 and 530 of the starting amount of protected, activated galactose (see Table 2), whereas the prior art method of Staveski et al. gave a yield of approximately 0.86% of the starting amount of protected, activated galactose.

TABLE 2

Yield Of Galactopyranoside-distearoylphosphatidylethanolainine

| | Yield | | | | |
|---|---|---|---|---|---|
| Compound | n = 3 | n = 5 | n = 7 | n = 10 | n = 16 |
| 1 | 100 | 100 | 100 | 100 | 100 |
| 2 | 87 | 89 | 81 | 82 | 90 |
| 3 | 63 | 72 | 69 | 66 | 76 |
| 4 | 83 | 82 | 81 | 91 | 95 |
| 5 | 82 | 69 | 72 | 75 | 81 |
| Overall | 37.3 | 36.3 | 32.5 | 36.9 | 52.6 | n = number of carbon atoms in a diol [i.e., $HO(CH_2)_nOH$] coupled to the saccharide at carbon 1.
Compound 1 = protected, activated saccharide, i.e., 1-chloro-2,3,4,6-tetra-O-benzylglucopyranoside.
Compound 2 = alcohol derivative of compound 1.
Compound 3 = aldehyde derivative of compound 2.
Compound 4 = protected, glycophospholipid conjugate.
Compound 5 = glycophospholipid conjugate.

For the synthesis of a glycophospholipid conjugate with mannose, the method of the invention gave a yield of between 15 and 23% of the starting amount of protected, activated mannose (see table 3), whereas with the prior art method of Staveski et al., a yield of approximately 4% of the starting amount of protected, activated mannose was obtained.

TABLE 3

Yield of Mannopyranoside-
distearoylphosphatidylethanolamine

| | Yield (%) | |
|---|---|---|
| | n = 10 | n = 6 |
| Compound 1 | 100 | 100 |
| Compound 2 | 52 | 41 |
| Compound 3 | 71 | 63 |
| Compound 4 | 88 | 89 |
| Compound 5 | 72 | 66 |
| Overall (1 → 5) | 23.4 | 15.2 | n = number of carbon atoms in a diol [i.e., $HO(CH_2)_nOH$] coupled to the saccharide at carbon 1.
Compound 1 = protected, activated saccharide, i.e., 1-chloro-2,3,4,6-tetra-O-benzylglucopyranoside.
Compound 2 = alcohol derivative of compound 1.
Compound 3 = aldehyde derivative of compound 2.
Compound 4 = protected, glycophospholipid conjugate.
Compound 5 = glycophospholipid conjugate.

This method of synthesis gave similar yields for different products having variable length of the spacer arm contained in the glycolipid conjugate.

The method of the invention produces glycophospholipid conjugates not only in high yields but also in a short time interval. For example, with the method of the invention, glycophospholipid conjugates can be synthesized within reaction times of approximately 20 hours. In contrast, prior art methods require approximately four days or more for completion of the synthesis of a phospholipid-saccharide conjugate. The efficiency of the method of the invention resides in the selection of the particular functional group for activation of the saccharide component, the choice of the particular reaction for conjugation, i.e., reductive amination, used for the interaction of phospholipid and saccharide as well as in the selection of catalysts and mild reaction conditions during the synthetic process.

Further, the method of the invention provides economy in its efficient utilization of reactant equivalencies. For example, in the method of the invention, phosphatidylethanolamine, an expensive reagent in the commercial marketplace, does not need to be added to excess. According to the present invention, the conjugation reaction proceeds efficiently with saccharide and phosphatidylethanolamine added at a molar equivalence ratio of approximately 1.0:1.5, respectively in contrast to prior art ratios of between approximately 1:4 and 1:48.

According to the present invention, glycophospholipid conjugates can be prepared in which the saccharide moiety is derived from a polysaccharide (glycan), for example, heparin, heparan sulfate, chondroitin sulfate, dermatan sulfate and derivatives thereof. In a particular embodiment of the invention, a heparin-phospholipid conjugate is synthesized. Heparin is primarily used as an anticoagulant and as an agent to regulate complement activity, angiogenesis, atherosclerosis and viral activity, and to stabilize and activate growth factors [Linhardt (1991) J. Chem. Ind. 4:45–50; Ornitz et al. (1995) Science 268:432–436]. Although efficacious by intravenous administration, heparin is ineffective when administered orally or transdermally [Faharn et al. (1996) Science 271:1116–1120; Zhou et al. (1992) in *Heparin and Related Polysaccharides* (Lan et al., eds.) Plenum Press, New York, pp. 141–152; Liu et al. (1994) J. Pharmaceutical Sciences 83:1034–1039]. However, enhanced adsorption of heparin via oral and transdermal routes may be effected by modifying the structure of heparin to increase its lipophilicity, for example, by preparing heparin-phospholipid conjugates of the invention. The heparin-phospholipid conjugates of the invention retain, and preferably enhance, the therapeutic activities of unconjugated heparin. In addition, hydrophobic heparin-phospholipid conjugates would also be useful as a coating for devices such as heart lung oxygenators, kidney dialyzers, etc., to maintain hemocompatibility [Larm et al. in *Heparin, Chemical and Biological Properties, Clinical Applications* (1989) (Lane and Lindahl, eds.) CRC Press, Boca Raton, Fla., pp. 597–608].

In a particular embodiment of the method of the invention is exemplified the synthesis of a nucleoside-phospholipid conjugate. As shown in FIG. 2, the starting nucleosidic reactant is 4', 5'-didehydro-5'-methoxy-adenosine. In the first step, the alcohol and amine groups are protected by benzylation under standard conditions. In the next step, an aldehyde is regenerated at the 5' position in the presence of dilute acid conditions. The resultant, aldehyde-functionalized saccharide moiety is interacted with distearoyl-phosphatidylethanolamine by reductive amination in the presence of sodium cyanoborohydride. The protecting groups are then removed to yield an adenosine-phosphatidylethanolamine conjugate.

In yet another particular embodiment of the method of the invention, the synthesis of a peptide-phospholipid conjugate is exemplified. The peptide, glycylserylglycylalanylvaline, protected at the seryl alcohol and valyl terminal carboxyl groups, is first interacted with 10-hydroxydecanoic acid in the presence of dicyclohexylcarbodiimide (DCC) and N-hydroxysuccinimide. The peptidyl alcohol is then oxidized to the corresponding aldehyde in the presence of pyridinium dichromate and nitrogen atmosphere. In the next step, the aldehyde-functionalized peptide is interacted with distearoyl-phosphatidylethanolamine by reductive amination in the presence of sodium cyanoborohydride. Removal of the protecting groups yields a peptide-phospholipid conjugate, i.e., distearoylphosphatidylethanolamine-glycylserylglycylalanylvaline.

Glycophospholipid and peptide-phospholipid conjugates of the present invention are particularly useful in the preparation of liposomes for utility as an in vivo liposomal drug- or therapeutic agent-delivery system. A drug or other agent can be incorporated ("loaded") into liposomes either passively (i.e., encapsulated during liposome formation) or actively (i.e., encapsulated after liposome formation). In general, hydrophobic drugs can be loaded directly into liposomes during vesicle formation, wherein the extent of uptake is a function of drug-lipid interactions and high trapping efficiencies are possible, depending on the solubility characteristics of the drug or agent in the liposomal membrane. In the case of water-soluble drugs, passive encapsulation depends on the ability of liposomes to trap aqueous buffer containing the solubilized drug during vesicle formation, and trapping efficiencies are generally less than 30%, being limited by the reduced volume trapped by the liposomes and the solubility index. Notably, water-soluble drugs that have protonizable amine functions can be actively taken up as a function of pH gradients [Mayer et al., 1993, in *Liposome Technology*, Vol. 2, edition 2 (Gregoriadis, ed.) CRC Press, Boca Raton, pp.27–44] and trapping efficiencies approaching 100% can result [Chonn et al. (1995) Current Opinion in Biotechnology 6:698–708].

The present invention contemplates the preparation of glycophospholipid and peptide-phospholipid conjugates prepared from phospholipid amphiphiles having varied compositions and structure. Modification of liposomal composition and/or structure, for example, through the utilization of specifically selected lipids, is known to result in the alteration or optimization of biological performance. For example, the utilization of monosialoganglioside $G_{M1}$ or poly-ethyleneglycol modified phosphatidyl ethanolamine (PEG-PE) in the preparation of liposomes results in the prolongation of liposomal circulation lifetimes [Allen et al. (1987) FEBS Lett. 223:42–46; Klibanov et al. (1990) FEBS Lett. 268:235–237; Blume et al. (1990) Biochim. Biophys. Acta (1990) 1029:91–97]. A prolonged circulation lifetime can also be achieved in liposomes loaded with a cytotoxic drug, e.g., doxorubicin [Bally et al. (1990) Biochim. Biophys. Acta 1023:133–139]. Further, it has been noted that such long-circulating liposomes containing PEG-PE or cytotoxic drugs accumulate in extravascular regions (e.g. within tumors) preferentially compared with conventional liposomes [Gabizon et al. (1988) Proc. Natl. Acad. Sci. 85:6949–6953; Wu et al. (1993) Cancer Res. 53:3765–3770; Papahadjopoulos et al. (1991) Proc. Natl. Acad. Sci. 88:11460–11464].

Also, membranes, liposomes, tubules and other self-assembled supramolecular systems can be prepared from glycophospholipids and protein-phospholipid conjugates of the invention in which the starting phospholipid amphiphiles comprise halogenated (e.g., fluorinated) hydrophobic tails. Fluorinated membrane systems show enhanced propensity to self-assemble, leading to increased membrane ordering and stability, which can significantly increase drug encapsulation stability [Riess (1995) J. Liposome Research 5:413–430]. Such fluorinated amphiphiles impact behavior in biological media and particle recognition, for example, reducing hemolytic activity, detergent activity, phospholipase activity, prolonging intravascular persistence, etc.

Liposomes can also be modified to contain surface-associated targeting information whereby resultant liposomes can be made specific for a designated cell type or tissue. For example, site-directing targeting ligands, such as monoclonal antibodies, can be attached to liposomes either covalently or non-covalently [Allen (1994) Trends Pharmacol. 15:215–220; Laukkanen et al. (1994) Biochemistry 33:11664–11670]. To date, antibodies [Lee et al. (1994) J. Biol. Chem. 269:3198–3204; Blume et al. (1993) Biochim. Biophys. Acta 1149:180–184; Maruyama et al. (1995) Biochim. Biophys. Acta 1234:74–80; and Allen et al. (1995) Biochim. Biophys. Acta 1237:99–108], glycolipids, e.g., galactose [Van Berkel et al. (1993) in *Liposome Technology*, Vol. 3, Edition 2 (Gregoriadis, ed.), CRC Press, Boca Raton, pp. 219–230] and mannose [Barratt et al. (1993) in *Liposome Technology*, Vol. 3, Edition 2 (Gregoriadis, ed.) CRC Press, Boca Raton, pp. 199–218], proteins, e.g., transferrin [Stavridis et al. (1986) Exp. Cell Res. 164:568–572] and asialofetuin [Hara et al. (1995) Gene 159:167–174], and vitamins, e.g., folic acid [Lee et al. (1995) Biochim. Biophys. Acta 1233:134–144] have been used to target specific cells via cell surface receptors. Also, improved therapeutic activity of liposomal drugs was obtained through the use of antibody-mediated targeting [Ahmad et al. (1993) Cancer Res. 53:1484–1488; Mori et al. (1995) Cancer Chemother. Pharmacol. 35:447–456].

The phospholipid conjugates of the present invention also comprise drugs or therapeutic agents such as antibiotics, chemotherapeutic agents, anti-inflammatory agents and the like. Literature on the feasibility of formulating liposomal drug delivery systems and the methods of preparation of such are readily available in the art, e.g., Wasan et al. (1995) Immunopharmacol. and Immunotoxicol. 17:1–15; Chonn et al. (1995) Current Opinion in Biotechnol. 6:698–708. It has been shown that liposomal drugs exhibit enhanced therapeutic activity and/or reduced toxicity compared to the corresponding free drug. In general, it is believed that altered pharmacokinetics for liposomal drugs lead to enhanced drug-bioavailability either to specific target cells, within the circulation, or to extravascular disease sites, e.g., tumors.

Liposomes prepared with glycophospholipid or peptide-phospholipid conjugates of the invention are also useful in gene therapy to transfer DNA through a membrane to a desired cellular location. The efficiency of the use of liposomes as delivery agents for DNA and other nucleosides, nucleotides, polynucleotides, etc. depends on such factors as tissue type, lipid membrane composition, ratio of lipid to DNA, stability of the DNA-lipid complex, etc. Recently, cationic lipids have been used as DNA delivery agents. Because the negative charges of a DNA backbone can interact with the positive charges of cationic lipids, DNA-liposome complexes are formed wherein the DNA can interact stably with the lipid on either the inside or outside of the liposome. The DNA may also become enclosed by the lipid and lie freely in the aqueous internal compartment, similar to encapsulation of toxic drugs. Because the positioning of DNA relative to the liposome depends on the composition and structure of the DNA-lipid complexes, the most effective method of DNA-lipid complex formation may be to design a specific complex for a 1:5 designated role, such as tissue targeting.

Glycophospholipid- and peptide-phospholipid-liposomes of the present invention can also be used to formulate a pharmaceutical composition useful for diagnosis, therapy, drug delivery, gene therapy, and other such indications. Such pharmaceutical compositions comprising glycophospholipid or peptide-phospholipid conjugates and a pharmaceutically acceptable carrier are effective in the therapeutic treatment of diseases, such as cancer, thrombosis, etc.

The glycophospholipid and peptide-phospholipid conjugates of the invention can be prepared in the form of their pharmaceutically acceptable salts. Pharmaceutically acceptable salts are salt derivatives of the disclosed phospholipid conjugates that retain the desired biological activity of the parent compound and do not impart undesired toxicological effects. Examples of such salts include, but are not limited by, salts formed with inorganic acids, for example, hydrochloric acid, hydrobromic acid, hydroiodic acid, sulfuric acid, phosphoric acid, nitric acid, and the like; and salts formed with organic acids, for example, acetic acid, oxalic acid, tartaric acid, succinic acid, maleic acid, fumaric acid, gluconic acid, citric acid, malic acid, ascorbic acid, benzoic acid, sulfonic acid and the like; and salts formed from elemental anions such as chloride, bromine and iodine.

Glycophospholipid and peptide-phospholipid conjugates can be combined with an inert pharmaceutical carrier to provide a pharmaceutical composition for medicinal and/or therapeutic use. The active ingredient of the pharmaceutical composition (i.e., glycophospholipid or peptide-phospholipid conjugate) should be included in an amount effective to accomplish the intended treatment or purpose. The pharmaceutical composition may further include such additives or stabilizing agents as water, buffers, serum albumen, ethanol, saccharide, high molecular weight polymers, starch, cellulose, talc, high molecular weight fatty acid, gelatine, agar, calcium phosphate, glycol, mannitol, etc.

Peptide-phospholipid and glycophospholipid conjugates of the invention are useful as synthetic vaccines. It has been recognized in the art [Wiesmuller et al. (1992) Int. J. Peptide Protein Res. 40:255–260] that conventional vaccination with attenuated virus may not lead to protection, since latent infection could be reactivated and immune deficiency develop even faster [Berzofsky (1991) FASEB J. 5:2412–2418]. Thus, synthetic vaccines are designed to avoid undesired side effects by limiting the number of epitopes to only the main epitopes which elicit neutralizing antibodies. Epitope-mapping techniques allow the routine and fast detection of the most important epitopes—peptide or saccharide. For peptide epitopes, multiple Merrifield peptide synthesis enables the production of a large number of overlapping free peptides for immunological assays. Methods for the synthesis of peptides and saccharides are well known in the art. See, for example, *Principles of Peptide Synthesis* 1984 (Bodanszky, ed.) Springer-Verlag, New York; *Peptides, Synthesis, Structures, and Applications*, 1995 (Gutte, ed.) Academic Press, New York; *Synthetic Peptides. A User's Guide*, 1992 (Grant, ed.) Freeman and Co., New York; *The Chemical Synthesis of Peptides*, 1991 (Jones, ed.) Clarendon Press, Oxford; etc.

In a particular embodiment, the present invention provides a synthetic vaccine based on a peptide-phospholipid conjugate wherein a phospholipid nitrogenous base is covalently joined to a peptide comprising a desired immunogenic epitope with formation of an ether linkage comprising a secondary or tertiary amine. In particular, an immunogenic peptide-phospholipid conjugate is prepared using phosphatidylethanolamine and an antigenic determinant of the epidermal growth factor receptor EGFR 516–529 synthesized by Merrifield peptide synthesis using Fmoc/tBu protection as described in Jung et al. (1985) Angew. Chem. 97:883–884; Angew. Chem Int. Ed. Engl. 24:872–873. The free amino terminal of the antigen is modified according to the method of the invention to contain an aldehyde group. The aldehyde-functionalized peptide is then reductively aminated by the phosphatidylethanolamine to form an immunogenic peptide-phospholipid conjugate. This lipopeptide immunogen elicits immunoprecipitating EGFR-specific polyclonal and monoclonal antibodies in vitro and in vivo according to the methods described in Jung et al. (1985) Angew. Chem. Int. Ed. Engl. 24:872–873; (1992) Angew. Chem. Int. Ed. Engl. 31:367:383; Metzger et al. (1992) Angew. Chem. Int. Ed. Engl. 31:226–228; Muller et al. (1988) The Lancet 1424–1425; Wiesmuller et al. (1992) Int. J. Peptide Protein Res. 40:255–260.

Glycophospholipid and peptide-phospholipid conjugates of the invention are useful as polymerizable amphiphiles (lipids modified to contain reactive groups at desired locations). Such reactive lipids comprise reactive groups such as diacetylenic, methancryloyl, acryloyl, dienoyl, sorbyl, lipoyl, styryl, etc., and are polymerized at temperatures above or below the Tm. Polymerized liposomes are utilized to prepare artificial membranes having amphiphilic backbones functionalized with carbohydrate and/or peptide binding sites and cross-linked by UV irradiation to form either a polymeric film or liposomes [see Charych et al. (1996) Chemtech 26:24–28; O'Brien "Trends in Polymers" (1994) 2:183–188; Chaikof (1996) Chemtech 26:17–22; Singh et al. (1995) *Novel Techniques in Synthesis and Processing of Advanced Materials* (Singh and Copley, eds.), The Minerals, Metals & Materials Society, pp. 177–186; Riess (1995) J. Liposome Research 5:413–430].

Artificial membranes prepared with glycophospholipid and/or peptide-phospholipid conjugates have utility as diagnostics and therapeutics. As diagnostics, these artificial membranes, resembling natural cell membranes in containing the capability of signalling molecular recognition, can do so by responding with a corresponding color change. For example, when an artificial bilayer carrying a specific viral or protein ligand binds to its complementary virus or protein molecule, the polymer backbone is deformed and the color changes from blue to red. As a therapeutic, glycophospholipid liposomes can interact with target analytes by displaying many copies of the biological ligand for binding. For example, many viruses, which are covered with sugar-binding proteins (lectins), form a tight association between a virus and the glycophospholipid liposome. Therefore, glycophospholipid liposomes can thwart viral binding to specific cell surfaces (e.g., erythrocytes which express sialic acid at their surfaces) by effectively competing with erythrocytes for viral binding. Thus, polymerized liposomes as artificial membranes are useful constructs for diagnostics (such as biosensor devices), for therapeutics (such as inhibitors of pathogen-cell interactions), for the preparation of a stable milieu (for example, for energy transduction), in surface modification, for the preparation and stabilization of organic zeolites, as substrates for medical implants and for growing cells, tissues and organs, etc.

The foregoing disclosure illustrates the various aspects of the invention. These include a composition of matter comprising a lipid-modified saccharide or peptide, including various glycophospholipid and peptide-phospholipid conjugates and methods of making and using such compositions. The addition of a phospholipid moiety to an immuno/biologically active saccharide or peptide results in the retention of the immuno/biological activity of the saccharide or peptide while altering the physical properties of the saccharide or peptide to permit its insertion into membrane structures and/or its incorporation into lipid-containing surface coatings in order to convey immuno/biological activity to membranes and surfaces. Such biological activity includes, without limitation, interaction with a cell receptor, promotion of cell adhesion or migration, and the like. The saccharide moiety can also incorporate a desired physical property, for example, the property of forming non-covalent bonding interactions with neighboring components as with, for example, growth-factors, cytokines, matrix proteins, and the like.

Also provided herein is a glycophospholipid- or peptide-phospholipid-containing particle having a surface comprising a phospholipid-modified saccharide or peptide, where the saccharide or peptide confers a biological activity upon the particle. Examples of a glycophospholipid- or peptide-phospholipid-containing particle include, without limitation, a liposome, a cell, a cell ghost, a micellar particle, and the like.

A lipid-modified molecule can have various properties of solubility, stability and specificity of interaction with lipid-containing surfaces and particles by proper selection of the lipid to be attached to the molecule. Exemplified herein are phospholipid-modified saccharides and peptides synthesized by nucleophilic reaction of said phospholipid with a functionalized saccharide or peptide. Methods of glycophospholipid and peptide-phospholipid conjugate synthesis are described herein. Methods for coupling an aldehyde-functionalized saccharide or peptide with an amine-derivatized phospholipid by reductive amination are described. Also described is a method of modifying the ether amine linker joining the phospholipid and saccharide or peptide moieties. The spacer arm serves to optimize saccharide or peptide bioactivity.

Utilities for the glycophospholipid and peptide-phospholipid conjugates of the present invention, as well as membranes, surfaces, and particles containing same, are useful for a wide variety of medical and biological applications. For example, glycophospholipid- and peptide-phospholipid-containing particles having desired receptor specificity are useful for targeting and drug delivery as well as for in situ gene therapy. Bioreactors having a desired activity incorporated on their surface can be used to activate or deactivate cells brought into contact therewith. Phenotypic cell modification can be accomplished by incorporating appropriate lipid-modified peptides as receptors or receptor ligands on the cell surfaces of the modified cells. Such modification can result in therapeutic applications for treatment of medical conditions arising from cell membrane or surface reactivity defects.

It will be apparent to those of ordinary skill in the art that alternative methods, reagents, procedures and techniques other than those specifically detailed herein can be employed or readily adapted to practice the methods of making and of using the phospholipid conjugates of the present invention. In particular, variations of the modifying lipid, of the saccharide or peptide to be modified, of the chemical reactions forming the modification, and of the types of materials that can be formed using the glycophospholipid and peptide-phospholipid conjugates of the invention are all deemed a part of the invention, accessible to those skilled in the art based upon the examples of the invention herein described. Such alternative methods, reagents, procedures and techniques are within the spirit and scope of this invention.

The methods and compositions of this invention are further illustrated in the following non-limiting Examples. All abbreviations used herein are standard abbreviations in the art. Specific procedures not described in detail in the Examples are well-known in the art.

EXAMPLES

Example 1
STARTING MATERIALS

The following compounds are either commercially available (source given in the parentheses) or easily prepared according to known methods. 1-chloro-2,3,4,6-tetra-O-benzyl-α-D-galactopyranoside prepared according to Iversen, T. and Bundle, D. R. *Carbohydr. Res.* (1982) 103:29; 1-chloro-2,3,4, 6-tetra-O-benzyl-α-D-glucopyranoside prepared according to Sinay, et al. *J. Am. Chem. Soc.* (1977) 99:6763); 1-chloro-2,3,4-tri-O-benzyl-α-L-fucopyranoside prepared according to Jacquinet, J.-C. and Sinay, P. J. Chem. Soc. Perkin I, (1979) 319); 1-ethyl-2,3, 4,6-tetra-O-benzyl-α-D-thiomanno-pyranoside (Dasgupta, F. and Garegg, P. J. *Acta Chem. Scandinavica*, (1989) 43:471); distearoyl phosphatidylethanolamine (Avanti); 1,3-propanediol (Aldrich); 1,10-decanediol (Aldrich); 1,16-hexadecanediol (Aldrich); cadmium carbonate (Aldrich); Pyridinium dichromate (Aldrich); sodium cyanoborohydride (Aldrich); 10% Palladium on carbon (Aldrich); hydrogen gas (Specialty Gas).

Example 2
SYNTHESIS OF A GLUCOPHOSPHOLIPID CONJUGATE (a) Coupling of 1-chloro-2,3,4,6-tetra-O-benzyl-α-D-glucopyranoside with 1,10-decanediol. The mixture of 1-chloro-2,3,4,6-tetra-O-benzyl-α-D-glucopyranoside (300 mg, 0.537 mmol), 1,10-decanediol (1.00 g, 5.74 mmol), $CdCO_3$ (0.10 g, 0.575 mmol) and $CaSO_4$ (0.50 g) was stirred in dry acetonitrile/toluene (1:2, 15 mL) at 65 °C. under a nitrogen atmosphere. TLC analysis (visualization by UV and char with 10% sulfuric acid in ethanol) of the reaction mixture indicated complete consumption of the carbohydrate starting material and the formation of a new carbohydrate derivative after 1.5 h. The reaction mixture was allowed to cool to room temperature. The organic layer was filtered with a toluene wash (20 mL), diluted with ethyl acetate (10 mL), washed with water (3×25 mL), dried over $MgSO_4$ and concentrated to an oil. Chromatographic purification (silica gel, 30% ethyl acetate in hexanes) afforded 0.324 g (0.465 mmol, 86%) of 10-(2,3,4,6-tetra-O-benzyl-β-D-glucopyranosyloxy)-n-decanol as a clear oil. $R_f$=0.25 (silica gel, 30% ethyl acetate in hexanes); $^1$H NMR ($CDCl_3$, 300 MHz) δ: 7.36 (m, 20H), 5.02 (t, J=10.5 Hz, 2H), 4.89 (d, J=9.0, 1H), 4.86 (d, J=9.0 Hz, 1H), 4.80 (d, J=10.8 Hz, 1H), 4.66 (d, J=8.4 Hz, 1H), 4.58 (dd, J=6.9, 4.8 Hz, 1H), 4.47 (d, J=7.8 Hz, 1H), 4.05 (m, 1H), 3.9–3.5 (m, 10H), 1.70 (m, 2H), 1.57 (m, 2H), 1.35 (m, 12H); MS (FAB+): 703.0 (($M+Li$)$^+$, 100), 611.0 (4), 455.0 (5), 423.1 (6), 261.1 (3), 181.1 (14), 160.0 (12).

(b) PDC oxidation of 10-(2,3,4,6-tetra-O-benzyl-β-D-glucopyranosyloxy)-n-decanol. Under an atmosphere of nitrogen, pyridinium dichromate (220 mg, 0.585 mmol) was added to a dry methylene chloride solution (6 mL) of 10-(2,3,4,6-tetra-O-benzyl-β-D-glucopyranosyloxy)-n-decanol (275 mg, 0.395 mmol). The resulting brown slurry was stirred at room temperature under nitrogen. TLC analysis (visualization by UV and char with 10% sulfuric acid in ethanol) of the reaction mixture indicated complete consumption of the starting material and the formation of a new compound after 16 h. The reaction mixture was treated with ether (10 mL), filtered through silica gel and Celite with an ether wash (25 mL) and concentrated to an off-white oil. Chromatographic purification (silica gel, 20% ethyl acetate in hexanes) afforded 204 mg (0.294 mmol, 74%) of 10-(2, 3,4,6-tetra-O-benzyl-β-D-glucopyranosyloxy)-n-decanal as a clear oil. $R_f$=0.40 (silica gel, 30% ethyl acetate in hexanes); $^1$H NMR ($CDCl_3$, 300 MHz) δ: 9.75 (t, J=1.8 Hz, 1H), 7.32 (m, 20H), 4.98 (dd, J=10.8, 9.6 Hz, 2H), 4.84 (t, J=10.5 Hz, 2H), 4.75 (d, J=10.8 Hz, 1H), 4.61 (d, J=8.4 Hz, 1H), 4.56 (dd, J=10.8, 6.0 Hz, 1H), 4.43 (d, J=7.8 Hz, 1H), 4.00 (m, 1H), 3.8–3.4 (m, 8H), 2.40 (dt, J=7.2, 1.5 Hz, 2H), 1.70 (m, 6H), 1.31, (m, 10H); MS (FAB+): 701.0 (($M+Li$)$^+$, 100), 609.0 (4), 455.0 (5), 423.1 (7), 181.1 (35), 160.0 (10), 107.0 (4), 105.0 (5).

(c) Reductive amination of 10-(2,3,4,6-tetra-O-benzyl-β-D-glucopyranosyloxy)-n-decanal with distearoyl phosphoethanolamine. Under a nitrogen atmosphere, sodium cyanoborohydride (20 mg, 0.318 mmol) was added in its solid form to a white slurry of DSPE (150 mg, 0.201 mmol) in methanol and chloroform (1:1, 10 mL) in the presence of molecular sieves (3 Å, 1.0 g). The mixture was stirred at 50° C. for 10 min to form a cloudy solution while gas was liberated from the reaction solution. To the above solution stirred at 50° C. was added dropwise 10-(2,3,4,6-tetra-O-benzyl-β-D-glucopyranosyloxy)-n-decanal (90 mg, 0.130 mmol) dissolved in methanol and chloroform (1:1, 5 mL). The clear solution was stirred for another 1.5 h while TLC analysis (visualization by UV, molybdenum blue reagent and char with 10% sulfuric acid in ethanol) indicated the complete consumption of the decanal starting material and the formation of a new compound. The reaction mixture was cooled to room temperature, filtered and concentrated to give a white solid. Chromatographic purification (silica gel, 150:12 of chloroform:methanol) afforded 158 mg (0.111 mmol, 85%) of the perbenzylated DSPE-decanylglucopyranoside conjugate as a waxy solid. $R_f$=0.33 (silica gel, 1:10 of methanol and chloroform); $^1$H NMR ($CDCl_3$, 300 MHz) δ: 10.05 (br s, 1H), 7.28 (m, 20H), 5.25 (m, 1H), 4.95 (d, J=8.4 Hz, 1H), 4.91 (d, J=8.1 Hz, 1H), 4.78 (t, J=10.2 Hz, 2H), 4.70 (d, J=11.1 Hz, 1H), 3.57 (d, J=9.9, 1H), 4.50 (m, 1H), 4.39 (m, 1H), 4.20 (m, 3H), 4.00 (m, 3H), 3.8–3.4 (m, 9H), 3.12 (br m, 2H), 2.85 (br m, 2H), 2.27 (q, J=7.5 Hz, 4H), 1.73 (m, 2H), 1.58 (m,4), 1.24 (s, 68H), 0.86 (t, J=6.6 Hz, 6H); MS (FAB+): 1426.3 ((M+H)$^+$, 2), 1180.1 (4), 904.4 (5), 840.1 (14), 728.3 (3), 607.4 (100), 395.3 (14), 341.3 927), 298.2 (23), 228.1 (34), 200.5 (16).

(d) Synthesis of distearoyl phosphoethanolamine-decanyl-β-D-glucopyranoside conjugate. Perbenzylated glucopyranoside-decanyl-DSPE conjugate (100 mg, 0.0701 mmol) was dissolved in chloroform (3 mL) and methanol (12 mL). The solution was stirred at room temperature in the presence of 10% palladium-carbon (Pd—C) (200 mg) under a hydrogen atmosphere. TLC analysis (visualization by UV, molybdenum blue reagent and char with 10% sulfuric acid in ethanol) of the reaction mixture indicated the complete consumption of the perbenzylated starting material and the formation of a new compound after 1 h. The reaction mixture was filtered through Celite with a chloroform/methanol (1:1, 10 mL) wash. Concentration and chromatographic purification (silica gel, 150:30:1 of $CHCl_3:MeOH:H_2O$) afforded 56 mg (0.0525 mmol, 75%) of distearoyl phosphatidylethanolamine-decanyl-β-glucopyranoside conjugate as a white solid. $R_f$=0.27 (silica gel, 150:30:1 of $CHCl_3:MeOH:H_2O$); $^1$H NMR ($CDCl_3$/$CD_3OD$ (v/v=2/1), 300 MHz) δ: 5.15 (m, 1H), 4.30 (d, J=2.1 Hz, 1H), 4.20 (d, J=7.8 Hz, 1H), 4.08 (m, 3H), 3.91 (m, 2H), 3.79 (m, 1H), 3.7–3.5 (m, 2H), 3.46 (m, 1H), 3.66 (m, 2H), 3.20 (m, 2H), 3.15 (br s, 2H), 2.92 (br t, J=7.8 Hz, 2H), 2.24 (q, J=7.2 Hz, 4H), 1.69 (m, 2H), 1.78 (s, 68H), 0.79 (t, J=6.9 Hz, 6H); MS (FAB+): 1066.8 ((M+H)$^+$, 15), 904.9 (4), 820.2 (7), 701.2 (6), 613.2 (10), 608.4 (100), 525.2 (15), 480.1 (31), 376.2 (50), 307.1 (93), 289.1 970), 242.1 (33), 228.1 (35), 214.1 (35).

Example 3
SYNTHESIS OF A GALACTOPHOSPHOLIPID CONJUGATE (a) (i) Coupling of 1-chloro-2,3,4,6-tetra-O-benzyl-α-D-galactopyranoside with 1,10-decanediol. The mixture of 1-chloro-2,3,4,6-tetra-O-benzyl-α-D-galactopyranoside (560 mg, 1.00 mmol), 1,10-decanediol (1.50 g, 8.61 mmol), $CdCO_3$ (0.20 g, 1.15 mmol) and $CaSO_4$ (0 .50 g) was stirred in dry acetonitrile/toluene (1:2, 15 mL) at 65° C. under a nitrogen atmosphere. TLC analysis (visualization by UV and char with 10% sulfuric acid in ethanol) of the reaction mixture indicated complete consumption of the carbohydrate starting material and the formation of a new carbohydrate derivative after 1.5 h. The reaction mixture was allowed to cool to room temperature. The organic layer was filtered with a toluene wash (20 mL), diluted with ethyl acetate (10 mL), washed with water (3×25 mL), dried over $MgSO_4$ and concentrated to an oil. Chromatographic purification (silica gel, 20% ethyl acetate in hexanes) afforded 0.570 g (0.818 mmol, 82%) of 10-(2,3,4,6-tetra-O-benzyl-β-D-galactopyranosyloxy)-n-decanol as a clear oil. $R_f$=0.44 (silica gel, 30% ethyl acetate in hexanes); $^1$H NMR ($CDCl_3$, 300 MHz) δ: 7.32 (m, 20H), 4.98 (dd, J=12, 4.5 Hz, 2H), 4.80 (d, J=10.5 Hz, 1H), 4.77 (d, J=4.8 Hz, 1H), 4.66 (d, J=11.8 Hz, 1H), 4.47 (d, J=4.5 Hz, 2H), 4.39 (d, J=10.5 Hz, 1H), 4.00 (m, 2H), 3.85 (dt, J=10.8, 1.8 Hz, 1H), 3.64 (t, J=6.9 Hz, 4H), 3.54 (m, 3H), 1.65 (m, 2H), 1.57 (m, 4H), 1.30 (br m, 12H); MS (FAB+): 703.1 ((M+Li)$^+$, 100), 511.2 (6), 455.1 (8), 423.2 (6), 397.2 (12), 181.1 (19), 160.0 (20), 149.0 (7);

(ii) Coupling of 1-chloro-2,3,4,6-tetra-O-benzyl-α-D-galactopyranoside with 1,16-hexadecanediol. The mixture of 1-chloro-2,3,4,6-tetra-O-benzyl-α-D-galactopyranoside (360 mg, 0.644 mmol), 1,16-hexadecanediol (1.00 g, 3.87 mmol), $CdCO_3$ (0.19 g, 1.09 mmol) and $CaSO_4$ (1.0 g) was stirred in dry acetonitrile/toluene (1:2, 15 mL) at 60° C. under a nitrogen atmosphere. TLC analysis (visualization by UV and char with 10% sulfuric acid in ethanol) of the reaction mixture indicated complete consumption of the carbohydrate starting material and the formation of a new carbohydrate derivative after 22 h. The reaction mixture was allowed to cool to room temperature. The organic layer was filtered with a toluene wash (20 mL), diluted with ethyl acetate (10 mL), washed with water (3×25 mL), dried over $MgSO_4$ and concentrated to an oil. Chromatographic purification (silica gel, 20 ethyl acetate in hexanes) afforded 0.455 g (0.583 mmol, 90%) of 16-(2,3,4,6-tetra-O-benzyl-β-D-galactopyranosyloxy)-n-hexadecanol as a clear oil. $R_f$=0.45 (silica gel, 30% ethyl acetate in hexanes); $^1$H NMR ($CDCl_3$, 300 MHz) δ: 7.35 (m, 20H), 4.96 (d, J=11.1 Hz, 2H), 4.85 (m, 1H), 4.75 (d, J=6.0 Hz, 1H), 4.64 (d, J=11.7 Hz, 1H), 4.45 (d, J=4.8 Hz, 2H), 3.38 (d, J=7.5 Hz, 1H), 4.0–3.8 (m, 4H), 3.7–3.5 (m, 7H), 1.79 (br s, 1H), 1.65 (m, 2H), 1.56 (m, 2H), 1.28 (m, 24 H); MS (FAB+): 787.3 ((M+Li)$^+$, 100), 423.2 (5), 253.1 (12), 181.1 (87), 160.0 (26), 136.0 (10), 107.0 (11).

(iii) Coupling of 1-chloro-2,3,4,6-tetra-O-benzyl-α-D-galactopyranoside with 1,3-propanediol. The mixture of 1-chloro-2,3,4,6-tetra-O-benzyl-α-D-galactopyranoside (560 mg, 1.00 mmol), 1,3-propanediol (0.760 g, 10.00 mmol), $CdCO_3$ (0.20 g, 1.15 mmol) and $CaSO_4$ (1.0 g) was stirred in dry acetonitrile/toluene (1:2, 15 mL) at 50° C. under a nitrogen atmosphere. TLC analysis (visualization by UV and char with 10% sulfuric acid in ethanol) of the reaction mixture indicated complete consumption of the carbohydrate starting material and the formation of a new carbohydrate derivative after 2.0 h. The reaction mixture was allowed to cool to room temperature. The organic layer was filtered with a toluene wash (20 mL), diluted with ethyl acetate (10 mL), washed with water (3×25 mL), dried over $MgSO_4$ and concentrated to an oil. Chromatographic purification (silica gel, 30–50% ethyl acetate in hexanes) afforded 0.520 g (0.870 mmol, 87%) of 3-(2,3,4,6-tetra-O-benzyl-β-D-galactopyranosyloxy)propanol as a clear oil. $R_f$=0.21 (silica gel, 50' ethyl acetate in hexanes) $^1$H NMR ($CDCl_3$, 300 MHz) δ: 7.30 (m, 20H), 4.96 (d, J=11.7 Hz, 1H), 4.83 (m, 1H), 4.75 (d, J=2.7 Hz, 2H), 4.63 (d, J=11.7 Hz, 1H), 4.42 (d, J=8.7 Hz, 1H), 4.38 (d, J=8.1 Hz, 1H), 4,05 (dt, J=9.6, 6.3 Hz, 1H), 3.90 (m, 2H), 3.84 (m, 1H), 3.73 (m, 4H), 3.56 (m, 4H), 2.43 (br s, 1H), 1.85 (sept, J=6.3 Hz, 2H); MS (FAB+): 605.2 ((M+Li)$^+$, 100), 513.2 (5), 423.2 (4), 181.1 (4), 160.0 (5).

(b) (i) PDC oxidation of 10-(2,3,4,6-tetra-O-benzyl-β-D-galactopyranosyloxy)-n-decanol. Under an atmosphere of nitrogen, pyridinium dichromate (460 mg, 1.222 mmol) was added to a dry methylene chloride solution (10 mL) of 10-(2,3,4,6-tetra-O-benzyl-β-D-galactopyrano-syloxy)-n-decanol (570 mg, 0.818 mmol). The resulting brown slurry was stirred at room temperature under nitrogen. TLC analysis (visualization by UV and char with 10% sulfuric acid in ethanol) of the reaction mixture indicated complete consumption of the starting material and the formation of a new compound after 20 h. The reaction mixture was treated with ether (10 mL), filtered through silica gel and Celite with an ether wash (25 mL) and concentrated to an off-white oil. Chromatographic purification (silica gel, 20% ethyl acetate in hexanes) afforded 374 mg (0.539 mmol, 66%) of 10-(2, 3,4,6-tetra-O-benzyl-β-D-galactopyranosyloxy)-n-decanal as a clear oil. $R_f$=0.61 (silica gel, 30% ethyl acetate in hexanes); $^1$H NMR ($CDCl_3$, 300 MHz) δ: 9.77 (t, J=1.5 Hz, 1H), 7.30 (m, 20H), 4.97 (dd, J=12.0, 2.7 Hz, 2H), 4.78 (d, J=11.1 Hz, 1H), 4.77 (d, J=4.5 Hz, 1H), 4.65 (d, J=12 Hz, 1H), 4.46 (d, J=4.2 Hz, 2H), 4.38 (d, J=7.8 Hz, 1H), 3.95 (m, 1H), 3.84 (dt, J=10.2, 1.8 Hz, 1H), 3.50 (m, 6H), 2.40 (dt, J=7.5, 1.8 Hz, 2H), 1.65 (m, 6H), 1.30 (m, 10 H); MS (FAB+): 701.0 ((M+Li)$^+$, 100), 455.1 (4), 181.1 (19), 160.0 (8).

(ii) PDC oxidation of 16-(2,3,4,6-tetra-O-benzyl-β-D-galactopyranosyloxy)-n-hexadecanol. Under an atmosphere of nitrogen, pyridinium dichromate (320 mg, 0.851 mmol) was added to a dry methylene chloride solution (6 mL) of 16-(2,3,4,6-tetra-O-benzyl-β-D-galactopyranosyloxy)-n-hexadecanol (455 mg, 0.583 mmol). The resulting brown slurry was stirred at room temperature under nitrogen. TLC analysis (visualization by UV and char with 10% sulfuric acid in ethanol) of the reaction mixture indicated complete consumption of the starting material and the formation of a new compound after 17 h. The reaction mixture was treated with ether (10 mL), filtered through silica gel and Celite with an ether wash (25 mL) and concentrated to an off-white oil. Chromatographic purification (silica gel, 10% ethyl acetate in hexanes) afforded 345 mg (0.443 mmol, 76%) of 16-(2,3,4,6-tetra-O-benzyl-β-D-galactopyranosyloxy)-n-hexadecanal as a clear oil. $R_f$=0.72 (silica gel, 30% ethyl acetate in hexanes); $^1$H NMR (CDCl$_3$, 300 MHz) δ: 9.75 (t, J=1.5 Hz, 1H), 7.30 (m, 20H), 4.95 (d, J=11.7 Hz, 2H), 4.75 (m, 2H), 4.63 (d, J=11.7 Hz, 1H), 4.43 (d, J=4.5 Hz, 2H), 4.36 (d, J=7.8 Hz, 1H), 3.65 (m, 2H), 3.82 (dt, J=8.7, 1.5 Hz, 1H), 3.56 (m, 6H), 2.40 (dt, J=7.5, 1.5 Hz, 2H), 1.60 (m, 4H), 1.26 (m, 24H); MS (FAB+): 801.3 (M+Na, 14), 785.3 ((M+Li)$^+$, 29), 253.1 (10), 181.1 (100), 160.0 (16), 136.0 (21), 123.0 (12).

(iii) PDC oxidation of 3-(2,3,4,6-tetra-O-benzyl-β-D-galacto-pyranosyloxy)propanol. Under an atmosphere of nitrogen, pyridinium dichromate (600 mg, 1.604 mmol) was added to a dry methylene chloride solution (10 mL) of 10-(2,3,4,6-tetra-O-benzyl-β-D-galactopyrano-syloxy)-n-decanol (520 mg, 0.870 mmol). The resulting brown slurry was stirred at room temperature under nitrogen. TLC analysis (visualization by UV and char with 10% sulfuric acid in ethanol) of the reaction mixture indicated complete consumption of the starting material and the formation of a new compound after 24 h. The reaction mixture was treated with ether (10 mL), filtered through silica gel and Celite with an ether wash (25 mL) and concentrated to an off-white oil. Chromatographic purification (silica gel, 20% ethyl acetate in hexanes) afforded 330 mg (0.554 mmol, 63%) of 3-(2,3,4,6-tetra-O-benzyl-β-D-galactopyranosyloxy)propanol as a clear oil. $R_f$=0.55 (silica gel, 30% ethyl acetate in hexanes); $^1$H NMR (CDCl$_3$, 300 MHz) δ: 9.82 (t, J=1.5 Hz, 1H), 7.35 (m, 20H), 5.00 (A of ABq, J=11.7 Hz, 1H), 4.88 (A of ABq, J=10.8 Hz, 1H), 4.77 (m, 2H), 4.70 (B of ABq, J=10.8 Hz, 1H), 4.48 (m, 1H), 4.43 (b of ABq, J=11.7 Hz, 1H), 4.25 (dt, J=9.9, 6.0 Hz, 1H), 3.95 (m, 2H), 3.85 (m, 1H), 3.60 (m, 4H), 2.75 (m, 2H); MS (FAB+): 603.1 ((M+Li)$^+$, 100), 511.2 (6), 455.1 (8), 423.2 (6), 397.2 (12), 181.1 (19), 160.0 (20), 149.0 (7).

(c) (i) Reductive amination of 10-(2,3,4,6-tetra-O-benzyl-β-D-galactopyranosyloxy)-n-decanal with distearoyl phosphoethanolamine. Under a nitrogen atmosphere, sodium cyanoborohydride (20 mg, 0.318 mmol) was added in its solid form to a white slurry of DSPE (200 mg, 0.267 mmol) in methanol and chloroform (1:1, 10 mL) in the presence of molecular sieves (3 Å, 800 mg). The mixture was stirred at 50° C. for 15 min to form a cloudy solution while gas was liberated from the reaction solution. To the above solution stirred at 50° C. was added dropwise 10-(2,3,4,6-tetra-O-benzyl-β-D-galactopyranosyloxy)-n-decanal (120 mg, 0.173 mmol) dissolved in methanol and chloroform (1:1, 5 mL). The clear solution was stirred for another 2 h while TLC analysis (visualization by UV, molybdenum blue reagent and char with 10% sulfuric acid in ethanol) indicated the complete consumption of the decanal starting material and the formation of a new compound. The reaction mixture was cooled to room temperature, filtered and concentrated to give a white solid. Chromatographic purification (silica gel, 150:12 of chloroform:methanol) afforded 228 mg (0.160 mmol, 92%) of the perbenzylated DSPE-decanyl-galactopyranoside conjugate as a waxy solid. $R_f$=0.47 (silica gel, 1:10 of methanol and chloroform); $^1$H NMR (CDCl$_3$, 300 MHz) δ: 10.20 (br s, 1H), 7.25 (m, 20H), 5.22 (m, 1H), 4.91 (dd, J=11.7, 2.7 Hz, 2H), 4.71 (m, 3H), 4.60 (q, J=11.7 Hz, 1H), 4.40 (d, J=4.8 Hz, 2H), 4.33 (m, 2H), 4.20 (m, 3H), 4.00 (m, 2H), 3.88 (m, 2H), 3.78 (t, J=7.8 Hz, 1H), 3.50 (m, 5H), 3.11 (br s, 2H), 2.85 (m, 2H), 2.27 (q, J=6.0 Hz, 4H), 1.70 (br s, 2H), 1.59 (br m, 6H), 1.24 (s, 70H), 0.86 (t, J=6.0 Hz, 6H); MS (FAD+): 1428.2 ((M+H)$^+$, 2), 904.2 (1), 840.0 (3), 607.3 (31), 341.1 (14), 240.0 (15), 228.1 (33), 181.0 (77), 136.0 (100), 116.9 (29).

(ii) Reductive amination of 16-(2,3,4,6-tetra-O-benzyl-β-D-galactopyranosyloxy)-n-hexadecanal with distearoyl phosphoethanolamine. Under a nitrogen atmosphere, sodium cyanoborohydride (20 mg, 0.318 mmol) was added in its solid form to a white slurry of DSPE (150 mg, 0.201 mmol) in methanol and chloroform (1:1, 10 mL) in the presence of molecular sieves (3 Å, 1.0 g). The mixture was stirred at 50° C. for 10 min to form a cloudy solution while gas was liberated from the reaction solution. To the above solution stirred at 50° C. was added dropwise 16-(2,3,4,6-tetra-0-benzyl-β-D-galactopyranosyloxy)-n-hexadecanal (100 mg, 0.128 mmol) dissolved in methanol and chloroform (1:1, 5 mL). The clear solution was stirred for another 1.5 h while TLC analysis (visualization by UV, molybdenum blue reagent and char with 10% sulfuric acid in ethanol) indicated the complete consumption of the decanal starting material and the formation of a new compound. The reaction mixture was cooled to room temperature, filtered and concentrated to give a white solid. Chromatographic purification (silica gel, 150:12 of chloroform:methanol) afforded 184 mg (0.122 mmol, 95%) of the perbenzylated DSPE-hexadecanyl-galactopyranoside conjugate as a waxy solid. $R_f$=0.44 (silica gel, 1:10 of methanol and chloroform); $^1$H NMR (CDCl$_3$, 300 MHz) δ: 9.80 (br s, 1H), 7.28 (m, 20H), 5.22 (m, 1H), 4.92 (dd, J=12.0, 1.5 Hz, 2H), 4.72 (m, 3H), 4.60 (d, J=11.7 Hz, 1H), 4.40 (d, J=4.8 Hz, 2H), 4.33 (d, J=7.8 Hz, 1H), 4.15 (m, 3H), 3.95 (m, 4H), 3.78 (dd, J=9.6, 7.8 Hz, 1H), 3.6–3.4 (m, 6H), 3.13 (br s, 2H), 2.87 (br m, 2H), 2.27 (q, J=7.2 Hz, 4H), 1.72 (br m, 2H), 1.57 (br m, 4H), 1.24 (s, 80H), 0.86 (t, J=6.9 Hz, 6H); MS (FAB+): 1511.4 ((M+H)$^+$, 0.24), 1264.9 (0.16), 828.3 (0.65), 607.5 (12), 550.5 (17), 284.3 (6), 91.0 (100).

(iii) Reductive amination of 3-(2,3,4,6-tetra-O-benzyl-β-D-galactopyranosyloxy)propanol with distearoyl phosphoethanolamine. Under a nitrogen atmosphere, sodium cyanoborohydride (20 mg, 0.318 mmol) was added in its solid form to a white slurry of DSPE (190 mg, 0.254 mmol) in methanol and chloroform (1:1, 10 mL) in the presence of molecular sieves (3 Å, 1.0 g). The mixture was stirred at 50° C. for 15 min to form a cloudy solution while gas was liberated from the reaction solution. To the above solution stirred at 50° C. was added dropwise 10-(2,3,4,6-tetra-O-benzyl-β-D-galactopyranosyloxy)-n-decanal (105 mg, 0.176 mmol) dissolved in methanol and chloroform (1:1, 5 mL). The clear solution was stirred for another 1.0 h while TLC analysis (visualization by UV, molybdenum blue reagent and char with 10% sulfuric acid in ethanol) indicated the complete consumption of the decanal starting material and the formation of a new compound. The reaction mixture was cooled to room temperature, filtered and concentrated to give a white solid. Chromatographic purification (silica gel, 150:12 of chloroform:methanol) afforded 195 mg (0.147 mmol, 83%) of the perbenzylated DSPE-propanyl-galactopyranoside conjugate as a waxy solid. $R_f$=0.50 (silica gel, 1:10 of methanol and chloroform); $^1$H NMR (CDCl$_3$, 300 MHz) δ: 9.50 (br s, 1H), 7.38 (m, 20H), 4.89 (br m, 1H), 4.92 (d, J=11.7 Hz, 1H), 4.80 (m, 2H), 4.70 (m, 2H), 4.60 (d, J=11.7 Hz, 1H), 4.47 (m, 1H), 4.42 (d, J=9.9 Hz, 2H), 4.35 (m, 1H), 4.11 (m, 2H), 3.95 (m, 4H), 3.77 (dd, J=9.3, 8.1 Hz, 1H), 3.57 (m, 6H), 2.97 (br s, 2H), 2.90 (br s, 2H), 2.25 (q, J=7.5 Hz, 4H), 2.10 (br m, 2H), 1.55 (br m, 4H), 1.25 (s, 54H), 0.89 (t, J=7.2 Hz, 6H); MS (FAB+): 1328.5 ((M+H)$^+$, 2), 722.6 (1), 626.3 (7), 349.2 (11), 239.1 (39), 223.1 (10), 131.1 (12), 117.0 (11), 104.0 (100).

(d) (i) Synthesis of distearoyl phosphoethanolamine-decanyl-β-D-galactopyranoside conjugate. Perbenzylated galactopyranoside-decanyl-DSPE conjugate (100 mg, 0.0701 mmol) was dissolved in chloroform (3 mL) and methanol (12 mL). The solution was stirred at room temperature in the presence of 10% Pd—C (200 mg) under a hydrogen atmosphere. TLC analysis (visualization by UV, molybdenum blue reagent and char with 10% sulfuric acid in ethanol) of the reaction mixture indicated the complete consumption of the perbenzylated starting material and the formation of a new compound after 1 h. The reaction mixture was filtered through Celite with a chloroform/methanol (1:1, 10 mL) wash. Concentration and chromatographic purification (silica gel, 150:30:1 of CHCl$_3$:MeOH:H$_2$O) afforded 56 mg (0.0525 mmol, 75%) of distearoyl phosphatidylethanolamine-decanyl-β-D-galactopyranoside conjugate as a white solid. $R_f$=0.33 (silica gel, 150:30:1 of CHCl$_3$:MeOH:H$_2$O); $^1$H NMR (CDCl$_3$/CD$_3$OD (v/v=2/1), 300 MHz) δ: 5.00 (m, 1H), 4.18 (dd, J=11.7, 3.0 Hz, 1H), 3.99 (d, J=6.9 Hz, 1H), 3.95 (m, 1H), 3.90 (m, 2H), 3.78 (t, J=6.0 Hz, 2H), 3.68 (m, 1H), 3.55 (d, J=6.0 Hz, 1H), 3.30 (m, 4H), 2.95 (br m, 2H), 2.74 (br t, 7.8 Hz, 2H), 2.10 (q, J=7.2 Hz, 4H), 1.48 (m, 2H), 1.37 (m, 6H), 1.03 (s, 70H), 0.65 (t, J=6.6 Hz, 6H); MS (FAB+): 1066.4 ((M+H)$^+$, 100), 905.5 (18), 890.0 (10), 800.4 (30), 768.2 (15), 723.4 (19).

(ii) Synthesis of distearoyl phosphoethanolamine-hexadecanyl-β-D-galactopyranoside conjugate. Perbenzylated galacto-pyranoside-hexadecanyl-DSPE conjugate (100 mg, 0.0701 mmol) was dissolved in chloroform (3 mL) and methanol (12 mL). The solution was stirred at room temperature in the presence of 10% Pd—C (200 mg) under a hydrogen atmosphere. TLC analysis (visualization by UV, molybdenum blue reagent and char with 10% sulfuric acid in ethanol) of the reaction mixture indicated the complete consumption of the perbenzylated starting material and the formation of a new compound after 0.5 h. The reaction mixture was filtered through Celite with a chloroform/methanol (1:1, 10 mL) wash. Concentration and chromatographic purification (silica gel, 150:30:1 of CHCl$_3$:MeOH:H$_2$O) afforded 62 mg (0.0539 mmol, 81%) of distearoyl phosphatidylethanolamine-hexadecanyl-β-D-galactopyranoside conjugate as a white solid. $R_f$=0.30 (silica gel, 150:30:1 of CHCl$_3$:MeOH:H$_2$O); $^1$H NMR (CDCl$_3$/CD$_3$OD (v/v=2/1), 300 MHz) δ: 5.17 (m, 1H), 4.33 (dd, J=12.0, 3.3 Hz, 1H), 4.14 (d, J=6.9 Hz, 1H), 4.08 (dd, J=12.0, 6.9 Hz, 1H), 4.00 (m, 2H), 3.92 (t, J=6.0 Hz, 2H), 3.81 (dt, J=6.0, 2.7 Hz, 2H), 3.69 (d, J=6.3 Hz, 2H), 3.45 (m, 4H), 3.10 (br m, 2H), 2.89 (dd, J=8.1, 8.1 Hz, 2H), 2.25 (q, J=8.4 Hz, 4H), 1.60 (m, 2H), 1.53 (m, 4H), 1.18 (s, 80H), 0.80 (t, J=6.9 Hz, 6H); MS (FAB+): 1156.5 ((M+Li)$^+$, 100), 1150.5 (M+H, 72), 988.6 (20), 905.0 (15), 711.3 (28).

(iii) Synthesis of distearoyl phosphoethanolamine-propanyl-β-D-galactopyranoside conjugate. Perbenzylated galactopyranoside-propanyl-DSPE conjugate (65 mg, 0.0489 mmol) was dissolved in chloroform (2 mL) and methanol (8 mL). The solution was stirred at room temperature in the presence of 10% Pd—C (40 mg) under a hydrogen atmosphere. TLC analysis (visualization by UV, molybdenum blue reagent and char with 10% sulfuric acid in ethanol) of the reaction mixture indicated the complete consumption of the perbenzylated starting material and the formation of a new compound after 2.0 h. The reaction mixture was filtered through Celite with a chloroform/methanol (1:1, 10 mL) wash. Concentration and chromatographic purification (silica gel, 150:30:1 of CHCl$_3$:MeOH:H$_2$O) afforded 38 mg (0.0393 mmol, 81%) of distearoyl phosphatidylethanolamine-propanyl-galactopyranoside conjugate as a white solid. $R_f$=0.21 (silica gel, 150:30:1 of CHCl$_3$:MeOH:H$_2$O); $^1$H NMR (CDCl$_3$/CD$_3$OD (v/v=2/1), 300 MHz) δ: 5.16 (m, 1H), 4.06 (br m, 4H), 3.93 (br m, 2H), 3.75 (br m, 4H), 3.46 (br m, 2H), 3.25 (br m, 4H), 2.46 (br s, 1H), 2.42 (br m, 4H), 2.00 (br m, 2H), 1.50 (br s, 4H), 1.17 (s, 54H), 0.79 (t, J=6.0 Hz, 6H); MS (FAB+): 1006.3 (M+K)$^+$, 990.3 (M+Na)$^+$, 968.4 ((M+H)$^+$, 53), 806.4 (15), 702.3 (30), 607.5 (100).

Example 4

SYNTHESIS OF A MANNOPHOSPHOLIPID CONJUGATE (a) Coupling of 1-ethyl-2,3,4,6-tetra-O-benzyl-α-D-thiomannopyranoside with 1,10-decanediol. Into a acetonitrile (50 mL) slurry of 1-ethyl-2,3,4,6-tetra-O-benzyl-α-D-thiomannopyranoside (1.20 g, 2.103 mmol) and 1,10-decanediol (1.80 g, 11.10 mmol) held at -40° C. under argon was added tris(p-bromophenyl)aminium hexachloroantimonate (2.58 g, 1.80 mmol). The resulting blue mixture was stirred for 2.0 h while the temperature was gradually warmed to 0° C. The resulting brown mixture was then filtered with an acetonitrile wash (10 mL), concentrated and purified by chromatography (silica gel, 30% ethyl acetate in hexanes) to afford 0.950 g (1.365 mmol, 65%) of 10-(2,3,4,6-tetra-O-benzyl-α-D-mannopyranosyloxy)-n-decanol as a clear oil. $R_f$=0.25 (silica gel, 30% ethyl acetate in hexanes); 1H NMR (CDCl$_3$, 300 MHz) δ: 7.40–7.15 (m, 20H), 4.89 (dd, J=10.2, 1.8 Hz, 2H), 4.74 (d, J=1.8 Hz, 1H), 4.68 (d, J=12.0 Hz, 1H) 4.63 (m, 2H), 4.53 (dd, J=12.0, 11.1 Hz, 2H), 4.05 (t, J=6.9 H, 1H), 3.98 (d, J=9.0 Hz, 1H), 3.90 (dd, J=9.0, 3.0 Hz, 1H), 3.78 (m, 3H), 3.66 (m, 1H), 3.59 (m, 3H), 3.45 (m, 1H), 1.52 (m, 4H), 1.29 (m, 10H); MS (FAB+): 703.1 ((M+Li)$^+$, 100), 613.1 (4), 455.1 (4), 423.1 (6), 223.1 (9), 16.0 (8).

(b) PDC oxidation of 10-(2,3,4,6-tetra-O-benzyl-α-D-mannopyranosyloxy)-n-decanol. Under an atmosphere of nitrogen, pyridinium dichromate (400 mg, 1.036 mmol) was added to a dry methylene chloride solution (10 mL) of 10-(2,3,4,6-tetra-O-benzyl-α-D-mannopyranosyloxy)-n-decanol (450 mg, 0.646 mmol). The resulting brown slurry was stirred at room temperature under nitrogen. TLC analysis (visualization by UV and char with 10% sulfuric acid in ethanol) of the reaction mixture indicated complete consumption of the starting material and the formation of a new compound after 15 h. The reaction mixture was treated with ether (10 mL), filtered through silica gel and Celite with an ether wash (25 mL) and concentrated to an off-white oil. Chromatographic purification (silica gel, 20% ethyl acetate in hexanes) afforded 345 mg (0.497 mmol, 77%) of 10-(2, 3,4,6-tetra-O-benzyl-α-D-mannopyranosyloxy)-n-decanal as a clear oil. $R_f$=0.50 (silica gel, 30% ethyl acetate in hexanes); $^1$H NMR (CDCl$_3$, 300 MHz) δ: 9.76 (dt, J=5.1, 1.5 Hz, 1H), 7.31 (m, 20H), 4.93 (d, J=6.6 Hz, 1H), 4.91 (d, J=2.4 Hz, 1H), 4.78 (d, J=2.1 Hz, 1H), 4.72 (d, J=12.0 Hz, 1H), 4.67 (m, 2H), 4.57 (dd, J=12.0, 10.8 Hz, 2H), 4.09 (t, J=6.9 Hz, 1H), 4.03 (d, J=9.3 Hz, 1H), 3.96 (dd, J=12.0, 2.7 Hz, 1H), 3.82 (m, 3H), 3.68 (m, 1H), 3.40 (dt, J=9.6, 6.6, Hz, 2H), 2.41 (dt, J=7.2, 1.8 Hz, 2H), 1.64 (m, 4H), 1.32 (m, 12H); MS (FAB+): 717.1 ((M+Na)$^+$, 33), 701.1 ((M+Li)$^+$, 100), 671.1 (8), 615.1 (7), 455.1 (12), 439.1 (10), 423.1 (20), 243.1 (10), 181.1 (17), 160.0 (20).

(c) Reductive amination of 10-(2,3,4,6-tetra-O-benzyl-α-D-mannopyranosyloxy)-n-decanal with distearoyl phosphoethanolamine. Under a nitrogen atmosphere, sodium cyanoborohydride (20 mg, 0.318 mmol) was added in its solid form to a white slurry of DSPE (170 mg, 0.227 mmol) in methanol and chloroform (1:1, 10 mL) in the presence of molecular sieves (3 Å, 1.0 g). The mixture was stirred at 50° C. for 10 min to form a cloudy solution while gas was liberated from the reaction solution. To the above solution stirred at 50° C. was added dropwise 10-(2,3,4,6-tetra-O-benzyl-α-D-mannopyranosyloxy)-n-decanal (100 mg, 0.144 mmol) dissolved in methanol and chloroform (1:1, 5 mL). The clear solution was stirred for another 1.5 h while TLC analysis (visualization by UV, molybdenum blue reagent and char with 10% sulfuric acid in ethanol) indicated the complete consumption of the decanal starting material and the formation of a new compound. The reaction mixture was cooled to room temperature, filtered and concentrated to give a white solid. Chromatographic purification (silica gel, 150:12 of chloroform:methanol) afforded 182 mg (0.127 mmol, 89%) of the perbenzylated DSPE-decanyl-mannopyranoside conjugate as a waxy solid. $R_f$=0.30 (silica gel, 1:10 of methanol and chloroform); $^1$H NMR (CDCl$_3$, 300 MHz) δ: 9.50 (br s, 1H), 7.4–7.1 (m, 20H), 5.25 (m, 1H), 4.88 (d, J=6.6 Hz, 1H), 4.87 (d, J=3.0 Hz, 1H), 7.74 (d, J=2.4 Hz, 1H), 4.68 (d, J=12.0 Hz, 1H), 4.63 (m, 1H), 4.55 (d, J=10.5, Hz, 1H), 4.51 (d, J=10.5, 1H), 4.41 (m, 2H), 4.20 (m, 3H), 4.00 (d, J=9.0 Hz, 3H), 3.93 (m, 1H), 3.76 (m, 3H), 3.65 (m, 2H), 3.36 (m, 2H), 3.12 (br m, 2H), 2.90 (br m, 2H), 2.29 (q, J=7.5 Hz, 4H), 1.76 (m, 2H), 1.26 (s, 68H), 0.89 (t, J=6.3 Hz, 6H); MS (FAB+): 1426.4 ((M+H)$^+$, 4), 1180.2 (6), 904.4 (8), 840.1 (14), 607.4 (100), 395.2 (12), 341.1 (23).

(d) Synthesis of distearoyl phosphoethanolamine-decanyl-α-D-mannopyranoside conjugate. Perbenzylated glucopyranoside-decanyl-DSPE conjugate (80 mg, 0.0561 mmol) was dissolved in chloroform (3 mL) and methanol (12 mL). The solution was stirred at room temperature in the presence of 10% Pd—C (160 mg) under a is hydrogen atmosphere. TLC analysis (visualization by UV, molybdenum blue reagent and char with 10% sulfuric acid in ethanol) of the reaction mixture indicated the complete consumption of the perbenzylated starting material and the formation of a new compound after 0.75 h. The reaction mixture was filtered through Celite with a chloroform/methanol (1:1, 10 mL) wash. Concentration and chromatographic purification (silica gel, 150:30:1 of CHCl$_3$:MeOH:H$_2$O) afforded 43 mg (0.0403 mmol, 72%) of distearoyl phosphatidylethanolamine-decanyl-β-D-glucopyranoside conjugate as a white solid. $R_f$=0.32 (silica gel, 150:30:1 of CHCl$_3$:MeOH:H$_2$O); $^1$H NMR (CDCl$_3$/CD$_3$OD (v/v=2/1), 300 MHz) δ: 5.16 (m, 1H), 4.42 (m, 1H), 4.36 (dd, J=12.0, 2.7 Hz, 1H), 4.06 (m, 3H), 3.92 (m, 2H), 3.78 (m, 2H), 3.69 (m, 3H), 3.60 (m, 1H), 3.45 (m, 1H), 3.33 (m, 1H), 3.14 (br m, 2H), 2.92 (br t, J=7.8 Hz, 2H), 2.25 (q, J=6.0 Hz, 4H), 1.60 (m, 2H), 1.52 (m, 4H), 1.19 (s, 68H), 0.80 (t, J=6.3 Hz, 6H); MS (FAB+): 1088.2 ((M+Na)$^+$, 7), 1072.2 ((M+Li)$^+$, 7), 1066.2 ((M+H)$^+$, 14), 607.4 (100), 480.0 (21), 459.1 (11), 395.2 (11), 376.1 (14), 341.2 (18), 298.1 (15), 228.1 (21), 200.5 (15).

Example 5

SYNTHESIS OF A FUCOPHOSPHOLIPID CONJUGATE (a) Coupling of 1-chloro-2,3,4-tri-O-benzyl-α-L-fucopyranoside with 1,10-decanediol. The mixture of 1-chloro-2,3,4-tri-O-benzyl-α-L-fucopyranoside (0.60 g, 1.324 mmol), 1,10-decanediol (1.75 g, 1.00 mmol), CdCO$_3$ (0.24 g, 0.1.395 mmol) and CaSO$_4$ (1.70 g) was stirred in dry acetonitrile/toluene (1:2, 15 mL) at 55–60° C. under a nitrogen atmosphere. TLC analysis (visualization by UV and char with 10% sulfuric acid in ethanol) of the reaction mixture indicated complete consumption of the carbohydrate starting material and the formation of a new carbohydrate derivative after 15 h. The reaction mixture was allowed to cool to room temperature. The organic layer was filtered with a toluene wash (20 mL), diluted with ethyl acetate (10 mL), washed with water (3×25 mL), dried over MgSO$_4$ and is concentrated to an oil. Chromatographic purification (silica gel, 30% ethyl acetate in hexanes) afforded 0.668 g (0.1.131 mmol, 85%) of 10-(2,3,4-tri-O-benzyl-β-L-fucopyranosyloxy)-n-decanol as a clear oil. $R_f$=0.58 (silica gel, 50% ethyl acetate in hexanes); $^1$H NMR (CDCl$_3$, 300 MHz) δ: 7.35 (m, 15H), 4.99 (d, J=6.3 Hz, 1H), 4.95 (d, J=5.4 Hz, 1H), 4.75 (m, 4H), 4.32 (d, J=7.8 Hz, 1H), 3.95 (m, 1H), 3.82 (dd, J=9.6, 7.8 Hz, 1H), 3.7–3.4 (m, 6H), 1.62 (m, 2H), 1.55 (m, 2H), 1.28 (s, 12H), 1.90 (d, J=6.3 Hz, 3H); MS (FAB+): 613.2 ((M+Na)$^+$, 2), 597.2 ((M+Li)$^+$, 100), 565.2 (2), 509.2 (3), 441.1 (6).

(b) PDC oxidation of 10-(2,3,4-tri-O-benzyl-β-L-fucopyranosyloxy)-n-decanol. Under an atmosphere of nitrogen, pyridinium dichromate (550 mg, 1.424 mmol) was added to a dry methylene chloride solution (20 mL) of 10-(2,3,4-tri-O-benzyl-β-L-fucopyranosyloxy)-n-decanol (580 mg, 0.982 mmol). The resulting brown slurry was stirred at room temperature under nitrogen. TLC analysis (visualization by UV and char with 10% sulfuric acid in ethanol) of the reaction mixture indicated complete consumption of the starting material and the formation of a new compound after 18 h. The reaction mixture was treated with ether (10 mL), filtered through silica gel and Celite with an ether wash (25 mL) and concentrated to an off-white oil. Chromatographic purification (silica gel, 20% ethyl acetate in hexanes) afforded 410 mg (0.697 mmol, 71%) of 10-(2,3,4-tri-O-benzyl-β-L-fucopyranosyloxy)-n-decanal as a clear oil. $R_f$=0.50 (silica gel, 30% ethyl acetate in hexanes); $^1$H NMR (CDCl$_3$, 300 MHz) δ: 9.76 (t, J=1.8 Hz, 1H), 7.35 (m, 15H), 5.02 (d, J=8.1 Hz, 1H), 4.98 (d, J=7.2 Hz, 1H), 4.81 (m, 2H), 4.76 (d, J=5.7 Hz, 1H), 4.72 (d, J=5.7 Hz, 1H); 3.34 (d, J=7.8 Hz, 1H), 3.97 (dt, J=9.6, 6.0 Hz, 2H), 3.84 (dd, J=9.6, 7.8 Hz, 1H), 3.65–3.40 (m, 3H), 2.41 (dt, J=7.2, 1.5 Hz, 2H), 1.65 9m, 4H), 1.31 (s, 10H), 1.21 (d, J=6.3 Hz, 3H); MS (FAB+): 611.2 ((M+Na)$^+$, 8), 595.2 ((M+Li)$^+$, 100), 567.2 (12), 505.2 (10), 441.1 (7), 401.1 (6).

(c) Reductive amination of 10-(2,3,4-tri-O-benzyl-β-L-fucopyranosyloxy)-n-decanal with distearoyl phosphoethanolamine. Under a nitrogen atmosphere, sodium cyanoborohydride (20 mg, 0.318 mmol) was added in its solid form to a white slurry of DSPE (170 mg, 0.227 mmol) in methanol and chloroform (1:1, 10 mL) in the presence of molecular sieves (3 Å, 1.0 g). The mixture was stirred at 50° C. for 10 min to form a cloudy solution while gas was liberated from the reaction solution. To the above solution stirred at 50° C. was added dropwise 10-(2,3,4-tri-O-benzyl-β-L-fucopyranosyloxy)-n-decanal (100 mg, 0.170 mmol)

dissolved in methanol and chloroform (1:1, 5 mL). The clear solution was stirred for another 1.0 h while TLC analysis (visualization by UV, molybdenum blue reagent and char with 10% sulfuric acid in ethanol) indicated the complete consumption of the decanal starting material and the formation of a new compound. The reaction mixture was cooled to room temperature, filtered and concentrated to give a white solid. Chromatographic purification (silica gel, 150:12 of chloroform:methanol) afforded 184 mg (0.140 mmol, 82%) of the perbenzylated DSPE-decanyl-fucopyranoside conjugate as a waxy solid. $R_f$=0.23 (silica gel, 1:10 of methanol and chloroform); $^1$H NMR (CDCl$_3$, 300 MHz) δ: 10.05 (br s, 1H), 7.27 (m, 15H), 5.23 (m, 1H), 4.95 (d, J=9.6 Hz, 1H), 4.91 (d, J=8.4 Hz, 1H), 4.8–4.6 (m, 4H), 4.37 (dd, J=12.0, 3.0 Hz, 1H), 4.28 (d, J=7.5 Hz, 1H), 4.18 (m, 3H), 3.98 (m, 2H), 3.88 (m, 1H), 3.70 (dd, J=9.3, 8.1 Hz, 1H), 3.6–3.5 (m, 4H), 3.11 (br s, 2H), 2.85 (br m, 2H), 2.26 (q, J=6.3 Hz, 4H), 1.70 (br s, 2H), 1.58 (br m, 4H), 1.23 (s, 68H), 1.50 (d, J=5.3 Hz, 3H), 0.86 (t, J=6.3 Hz, 6H); MS(FAB+):1332.1((M+2Li-H)$^+$, 24.4), 717.3 (14), 622.2 (100), 433.2 (76), 230.1 (53) 181.1 (40), 161.0 (58), 107.0 (59).

(d) Synthesis of distearoyl phosphoethanolamine-decanyl-β-L-fucopyranoside conjugate. Perbenzylated fucopyranoside-decanyl-DSPE conjugate (100 mg, 0.0750 mmol) was dissolved in chloroform (4 mL) and methanol (12 mL). The solution was stirred at room temperature in the presence of 10% Pd—C (200 mg) under a hydrogen atmosphere. TLC analysis (visualization by UV, molybdenum blue reagent and char with lo- sulfuric acid in ethanol) of the reaction mixture indicated the complete consumption of the perbenzylated starting material and the formation of a new compound after 1.5 h. The reaction mixture was filtered through Celite with a chloroform/methanol (1:1, 10 mL) wash. Concentration and chromatographic purification (silica gel, 150:30:1 of CHCl$_3$:MeOH:H$_2$O) afforded 56 mg (0.0532 mmol, 71%) of distearoyl phosphatidylethanolamine-decanylβ-L-fucopyranoside conjugate as a white solid. $R_f$=0.25 (silica gel, 150:30:1 of CHCl$_3$:MeOH:H$_2$O); $^1$H NMR (CDCl$_3$/CD$_3$OD (v/v=2/1), 300 MHz) δ: 5.19 (m, 1H), 4.36 (dd, J=12.0, 2.7 Hz, 1H), 4.13 (m, 4H), 3.95 (m, 2H), 3.80 (m, 1H), 3.70 (m, 1H), 3.55 (m, 2H), 3.46 (m, 2H), 3.17 (br s, 2H), 3.44 (br t, J=8.1 Hz, 2H), 2.27 (q, J=6.9 Hz, 4H), 1.70 (m, 2H), 1.55 (m, 4H), 1.25 (d, J=6.9 Hz, 3H), 1.24 (s, 68H), 0.83 (t, J=6.9 Hz, 6H); MS (FAB+): 1116.2 ((M+3Na)$^+$, 12), 1169.0 ((M+3Li)$^+$, 10), 1035.3 (12), 993.3 (27), 989.3 (27), 982.4 (39), 963.3 (30), 854.4 (60), 848.7 (100).

Example 6
PREPARATION OF LIPOSOMES FROM GLYCOPHOSPHOLIPID CONJUGATES

Glycophospholipid conjugates prepared according to the present invention are used as the starting material for the preparation of liposomes. Liposomes can be prepared by a variety of method [Gregoriadis, Liposome preparation and related techniques (1993) in *Liposome Technology*, Vol. 1, edition 2 (Gregoriadis, ed.) CRC Press, Boca Raton, pp. 1–63; Watwe et al. (1995) Curr. Sci. 68:715–724]. Methods for making liposomes from glycophospholipid conjugates are known in the art, e.g., Szoka et al. (1980) Ann. Rev. Biophys. Bioeng. 9:467; Willschut in Liposome Methodology (Laserman and Barbet, eds.) INSERM, Paris (1982) p.11. The preparation of liposomal vesicles from galactosylated lipids is described in Haensler et al. (1991) Glycoconjugate J. 8:116–124.

Example 7
PREPARATION AND USE OF GLYCOPHOSPHOLIPID LIPOSOMES AS DRUG DELIVERY SYSTEMS Drug delivery systems prepared from glycophospholipid conjugates of the present invention are formulated according to the considerations put forth in Wasan et al. (1995) Immunopharmacol. Immunotoxicol. 17:1–15, and Chonn et al. (1995) Current Opinion in Biotechnology 6:698–708. Glycophospholipid liposomes are prepared according to prior art methods used to prepare various liposomal formulations useful as drug carrier vehicles. These methods are modified according to considerations known in the art to compensate for the chemical and physical characteristics imposed by the glycophospholipid component of liposomes prepared from the glycophospholipid conjugates of the present invention. Examples of methods used to prepare liposomes used for targeted drug delivery and/or therapy include, but are not limited to: Allen et al. (1995) Biochim. Biophys Acta 1237:99–108; Ahmad et al. (1993) Cancer Res. 53:1484–1488; Mori et al. (1995) Cancer Chemother. Pharmacol. 35:447–456; Van Berkel et al. (1993) in Liposome Technology Volume 3, Edition 2 (Gregoriadis, ed.) CRC Press, Boca Raton, pp. 219–230; Mitsutake et al. (1994) Mycopathologia 128:13–17; Oku et al. (1994) Int. J. Cancer 58:415–419.

Example 8
PREPARATION AND USE OF GLYCOPHOSPHOLIPID LIPOSOMES FOR DNA DELIVERY SYSTEMS Methods for liposome preparation for use as DNA delivery systems are readily available in the art. See, for example, Ledley (1994) Current Opinion in Biotechnology 5:626–636 and the review articles by Smith et al. (1993) Biochim. Biophys. Acta 1154:327–340 and Chonn et al. (1995) Current Opinion in Biochemistry 6: 698–708, wherein methods are described for liposome preparation from: (a) pre-formed cationic liposomes; (b) resuspension of dried lipid; (c) dilution of a proliposome mixture to give liposome dispersions; (d) coating of the DNA; and (e) charged lipid particles. To prepare liposomes from glycophospholipid conjugates of the invention for use in DNA delivery, the molecular properties of the glycophospholipid conjugates and their effects on the resultant structural form of the liposomes is considered and appropriate modifications as are known in the art are made to accommodate the physical and chemical properties introduced by the glycophospholipid component. Examples of methods used to prepare liposomes for DNA delivery systems include, but are not limited to: Stavridis et al. (1986) Exp. Cell Res. 164:568–572; Farhood et al. (1995) Biochim. Biophys. Acta 1235:289–295; Hara et al. (1995) Gene 159:167–174, etc.

Example 9
SYNTHESIS OF A NUCLEOSIDE-PHOSPHOLIPID CONJUGATE.

The synthesis is presented schematically in FIG. 2.
(a) Protection of 4',5'-didehydro-5'-methoxy-adenosine. The exemplified nucleoside is 4',5'-didehydro-5'-methoxy-adenosine, a known third generation inhibitor of S-adenosylhomocysteine hydrolase [Yuan et al. (1996) Advances in Antiviral Drug Design 241–88]; it may be substituted with a desired nucleoside, nucleotide, polynucleotide, DNA, RNA, etc.

Methods useful in the protection of functional groups of compounds are well known in the art, e.g., see *Protective Groups in Organic Synthesis*, Second edition (T. W. Greene and P. G. M. Wuts, eds.) John Wiley & Sons, New York, 1991, Chapter 2, and references contained therein. For example, the functional alcohol and amine groups of 4',5'-didehydro-5'-methoxy-adenosine are benzylated by stirring the starting compound with benzyl bromide in the presence of sodium hydride.

(b) Generation of a functional aldehyde group on the saccharide moiety.

(i) Preparation of 1-N,2'3'-O-tribenzyl-5'-oxy-adenosine. 1-N,2'3'-O-tribenzyl-4',5'-didehydro-4'-methoxy-adenosine is exposed to dilute acid, e.g., HCl, conditions to generate an aldehyde group at the 5' position. Reaction conditions are provided, for example, in the method described in Boechman Jr. et al. (1979) J. Org. Chem. 44:4781.

(ii) Preparation of 5'-(1-N,2',3'-O-tribenzyl-adenosyloxy)-n-decanal. The starting nucleoside or a functionalized derivative thereof (e.g., 5'-bromo-derivative) can be modified to comprise an alcohol having a hydrocarbon chain of variable length [Brown et al. (1964) J. Amer. Chem. Soc. 86:1089; Cason et al. (1961) J. Org. Chem 26:3645]. For example, 1-N,2',3'-O-tribenzyl-5'-bromo-adenosine is reacted with 1,10-decanediol in the presence of $CdCO_3$ and $CaSO_4$ under a nitrogen atmosphere using the protocol essentially as described in Example 2(a) to produce 5'-(1-N,2',3'-O-tribenzyl-adenosyloxy)-n-decanol.

The alcohol product is then oxidized in the presence of pyridinium chromate under a nitrogen atmosphere to the corresponding aldehyde derivative, i.e., 5'-(1-N,2',3'-O-tribenzyl-adenosyloxy)-n-decanal, using the protocol essentially as described in Example 2(b).

(c) Reductive amination of 1-N,2',3'-O-tribenzyl-4'-oxy-adenosine, or its 5'-(1-N,2',3'-O-tribenzyl-adenosyloxy)-n-decanal derivative, with distearoylphosphatidylethanolamine (DSPE). The procedure used is as essentially described in Example 2(c). Under a nitrogen atmosphere, sodium cyanoborohydride is added in its solid form to a white slurry of DSPE in methanol and chloroform (1:1) in the presence of molecular sieves (3 Å). The mixture is stirred at 50° C. for 10 minutes to form a cloudy solution while gas is liberated from the reaction solution. To the above solution stirred at 50° C. is added dropwise 1-N,2',3'-O-tribenzyl-4'-oxy-adenosine or 5'-(1-N,2',3'-O-tribenzyl-adenosyloxy)-n-decanal dissolved in methanol and chloroform (1:1). The solution is stirred for approximately an hour while TLC analysis (visualization by UV, molybdenum blue reagent and char with 10l sulfuric acid in ethanol) indicates the complete consumption of the decanal starting material and the formation of a new compound. The reaction mixture is cooled to room temperature, filtered and concentrated. Chromatographic purification (silica gel, 150:12 of chloroform:methanol) affords a yield of DSPE-1-N,2',3'-O-tribenzyladenosine conjugate and the DSPE-decanyl-1-N,2',3'-O-tribenzyladenosine conjugate, respectively.

(d) Synthesis of distearoyl phosphatidylethanolamine-adenosine or distearoyl phosphatidylethanolamine-decanyl-adenosine conjugate. The procedure used is as essentially described in Example 2(d). DSPE-1-N,2',3'-O-tri-benzyl-adenosine or DSPE-decanyl-1-N,2',3'-O-tribenzyl-adenosine conjugate is dissolved in chloroform and methanol. The solution is stirred at room temperature in the presence of 10% palladium on carbon (Pd—C) under a hydrogen atmosphere. TLC analysis (visualization by UV, molybdenum blue reagent and char with 10% sulfuric acid in ethanol) of the reaction mixture indicates the complete consumption of the protected starting material and the formation of a new compound after approximately 1.5 hours. The reaction mixture is filtered through Celite with a chloroform/methanol (1:1) wash. Concentration and chromatographic purification (silica gel, 150:30:1 of $CHCl_3$:MeOH:$H_2O$) affords a yield of distearoyl phosphatidylethanolamine-adenosine or distearoyl phosphatidylethanolamine-decanyl-adenosine conjugate, respectively.

Example 10

SYNTHESIS OF A PEPTIDE-PHOSPHOLIPID CONJUGATE.

The synthesis is presented schematically in FIG. 3.

Functional groups, other than the terminal amino group, of a peptide (for example, gly-ser-gly-ala-val) are protected by methods known in the art, for example, methylation of the terminal carboxy group by the method of Ananthara-maiah et al. (1977) J. chem. Soc. PERKIN 1 490–491 and the hydroxyl and carboxyl groups may be benzylated according to the methods described in Protective Groups in Organic Synthesis, Second edition (T. W. Greene and P. G. M. Wuts, eds.) John Wiley & Sons, New York, 1991, Chapter 2, and references contained herein.

(a) Coupling of glycylserylglycylaspartylvaline with 1,10-decanediol. The protected peptide is reacted with 10-hydroxydecanoic acid (Aldrich) in the presence of dicyclohexylcarbodiimide (DCC) (Aldrich) and N-hydroxysuccinimide (Aldrich) according to Bergeron et al. (1981) J. Org. Chem. 46:4524, until the complete consumption of the peptide starting material is confirmed by thin layer chromatography. Flash column purification gives 10-(peptidyloxy) decanol as product, through formation of an amide linkage.

(b) PCD oxidation of 10-(O-benzyl-glycylserylglycylaspartylvalyloxy)-n-decanol. The procedure used is as essentially described in Example 2(b). Under an atmosphere of nitrogen, pyridinium dichromate is added to a dry methylene chloride solution of 10-(O-benzyl-glycylserylglycylapartylvalyloxy)-n-decanol. The resulting slurry is stirred at room temperature under nitrogen. TLC analysis (visualization by UV and char with 10% sulfuric acid in ethanol) of the reaction mixture indicates complete consumption of the starting material and the formation of a new compound after approximately 16 hours. The reaction mixture is treated with ether, filtered through silica gel and Celite with an ether wash, and concentrated. Chromatographic purification (silica gel, 20% ethyl acetate in hexanes) affords a yield of 10-(O-benzyl-glycylserylglycylaspartylvalyloxy)-n-decanal.

(c) Reductive amination of 10-(O-benzyl-glycylserylglycylaspartylvalyloxy)-n-decanal with distearoyl phosphatidylethanolamine (DSPE). The procedure used is as essentially described in Example 2(c). Under a nitrogen atmosphere, sodium cyanoborohydride is added in its solid form to a white slurry of DSPE in methanol and chloroform (1:1) in the presence of molecular sieves (3 Å). The mixture is stirred at 50° C. for 10 minutes to form a cloudy solution while gas is liberated from the reaction solution. To the above solution stirred at 50° C. is added dropwise 10-(O-benzyl-glycylserylglycylaspertylvalyloxy)-n-decanal dissolved in methanol and chloroform (1:1). The clear solution is stirred for approximately 1.5 hours while TLC analysis (visualization by UV, molybdenum blue reagent and char with 10% sulfuric acid in ethanol) indicates the complete consumption of the decanal starting material and the formation of a new compound. The reaction mixture is cooled to room temperature, filtered and concentrated. Chromatographic purification (silica gel, 150:12 of chloroform:methanol) affords a yield of the protected DSPE-decanyl-peptide conjugate.

(d) Synthesis of distearoylphosphatidylethanolamine-decanyl-glycylserylglycylaspartylvaline conjugate. The procedure used is as essentially described in Example 2(d) (see also Jackson et al. (1976) Synthesis 685–687). DSPE-decanyl-O-benzyl glycylserylglycylaspartylvaline conjugate is dissolved in chloroform and methanol. The solution is stirred at room temperature in the presence of 10% palladium-carbon (Pd—C) under a hydrogen atmosphere. TLC analysis (visualization by UV, molybdenum blue reagent and char with 10% sulfuric acid in ethanol) of the reaction mixture indicates the complete consumption of the protected starting material and the formation of a new compound after approximately one hour. The reaction mixture is filtered through Celite with a chloroform/methanol (1:1)wash. Concentration and chromatographic purification (silica gel, 150:30:1 of CHCl$_3$:MeOH:H$_2$O) affords a yield of distearoyl phosphatidylethanolamine-decanyl-peptide conjugate.

We claim:

1. A self-assembling system comprising a glycophospholipid or a peptide-phospholipid conjugate, having a phospholipid moiety and a saccharide or peptide moiety joined by a diether linkage comprising a secondary or tertiary amine, said conjugate having the formula

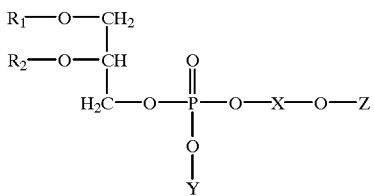

wherein

R$_1$ and R$_2$ are independently selected from the group comprising straight or branched, unsubstituted or substituted, saturated or unsaturated acyl, alkyl, alkenyl, alkynyl and aryl groups;

Y is a cation;

X is a secondary or tertiary amine linker, comprising two to twenty carbon atoms, wherein a substituent group of the amine is selected independently from a group comprising a hydrogen, a straight or branched, unsubstituted or substituted alkyl, alkenyl, alkynyl and aryl groups; and Z is a saccharide, a peptide or a functionalized derivative thereof; and a member selected from the group consisting of a membrane, a bilayer, a film, a liposome and a carrier-vehicle.

2. The self-assembling system of claim 1 wherein said which is a substrate for medical implants or for growing cells and/or organs.

3. A liposome comprising a glycophospholipid or a peptide-phospholipid conjugate, having a phospholipid moiety and a saccharide or peptide moiety joined by a diether linkage comprising a secondary or tertiary amine, said conjugate having the formula

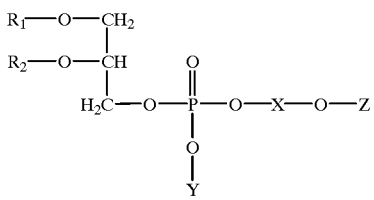

wherein

R$_1$ and R$_2$ are independently selected from the group comprising straight or branched, unsubstituted or substituted, saturated or unsaturated acyl, alkyl, alkenyl, alkynyl and aryl groups;

Y is a cation;

X is a secondary or tertiary amine linker, comprising two to twenty carbon atoms, wherein a substituent group of the amine is selected independently from a group comprising a hydrogen, a straight or branched, unsubstituted or substituted alkyl, alkenyl, alkynyl and aryl groups; and Z is a saccharide, a peptide or a functionalized derivative thereof.

4. The liposome of claim 3 further comprising a drug or therapeutic agent.

5. The liposome of claim 3 wherein said drug or therapeutic agent is selected from the group comprising, an antibiotic, a chemotherapeutic agent and an anti-inflammatory agent.

6. The liposome of claim 4 wherein said drug or therapeutic agent is a diagnostic.

7. The liposome of claim 3 which is specific for a designated cell or tissue.

8. The liposome of claim 4 wherein said drug or therapeutic agent is a protein or a DNA.

9. The liposome of claim 8 wherein said protein is a monoclonal antibody.

10. A pharmaceutical composition comprising the liposome of claim 4 and a pharmaceutically acceptable carrier.

11. A method for producing a glycophospholipid or peptide-phospholipid conjugate having a phospholipid moiety and a saccharide or peptide moiety joined by a diether linkage comprising a secondary or tertiary amine, said conjugate having the formula

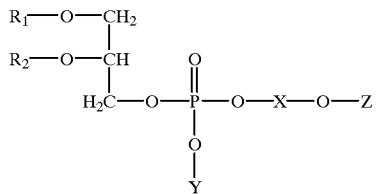

wherein

R$_1$ and R$_2$ are independently selected from the group comprising straight or branched, unsubstituted or substituted, saturated or unsaturated acyl, alkyl, alkenyl, alkynyl and aryl groups;

Y is a cation;

X is a secondary or tertiary amine linker, comprising two to twenty carbon atoms, wherein a substituent group of the amine is selected independently from a group comprising a hydrogen, a straight or branched, unsubstituted or substituted alkyl, alkenyl, alkynyl and aryl groups; and Z is a saccharide, a peptide or a functionalized derivative thereof; said method comprising the step of combining a phospholipid nitrogenous base with an aldehyde-functionalized saccharide or peptide derivative under conditions sufficient to form said glycophospholipid or peptide-phospholipid conjugate.

12. The method of claim 11 further comprising a reducing agent.

13. The method of claim 12 wherein said reducing agent is sodium cyanoborohydride.

14. The method of claim 11 wherein said phospholipid nitrogenous base, naturally occurring or synthetic, contains a free —NH— group.

15. The method of claim 11 wherein said phospholipid nitrogenous base comprises from two to eighteen carbon atoms.

16. The method of claim 11 wherein said phospholipid nitrogenous base is phosphatidylethanolamine.

17. The method of claim 11 wherein said aldehyde-functionalized saccharide or peptide derivative has the formula $$Z-O-(CH_2)_{n-1}-CHO \text{ or } Z-(OCH_2CH_2)_{m-1}-CHO$$

wherein n=1–18, m=3–250, and Z=a saccharide, peptide or a functionalized derivative thereof.

18. The method of claim 11 wherein said saccharide is selected from the group consisting of a monosaccharide, a disaccharide, an oligosaccharide and a polysaccharide or is selected from the group consisting of a nucleoside, a nucleotide, polynucleotide, a DNA and an RNA.

19. The method of claim 11 further comprising the earlier steps of:

reacting an activated saccharide or peptide derivative with a diol, and transforming the resultant primary hydroxyl group to said aldehyde-functionalized saccharide or peptide derivative.

20. The method of claim 19 wherein said diol has the general formula $$HO(CH_2)_nOH \text{ or } H-(OCH_2CH_2)_m-OH$$

wherein n=1–18 and m=3–250.

* * * * *

UNITED STATES PATENT AND TRADEMARK OFFICE
CERTIFICATE OF CORRECTION

PATENT NO. : 6,171,614 B1
DATED : January 9, 2001
INVENTOR(S) : Chikof et al.

It is certified that error appears in the above-identified patent and that said Letters Patent is hereby corrected as shown below:

Claim 2, column 33,
Line 47, delete "wherein said".

Signed and Sealed this

Ninth Day of October, 2001

*Attest:*

NICHOLAS P. GODICI
*Attesting Officer*    *Acting Director of the United States Patent and Trademark Office*